US010093697B2

(12) United States Patent
Gillberg et al.

(10) Patent No.: US 10,093,697 B2
(45) Date of Patent: *Oct. 9, 2018

(54) IBAT INHIBITORS FOR THE TREATMENT OF LIVER DISEASES

(71) Applicant: Albireo AB, Gothenburg (SE)

(72) Inventors: Per-Göran Gillberg, Mölndal (SE); Hans Graffner, Helsingborg (SE); Ingemar Starke, Gothenburg (SE)

(73) Assignee: Albireo AB

( * ) Notice: Subject to any disclaimer, the term of this patent is extended or adjusted under 35 U.S.C. 154(b) by 0 days.

This patent is subject to a terminal disclaimer.

(21) Appl. No.: 15/726,203

(22) Filed: Oct. 5, 2017

(65) Prior Publication Data

US 2018/0030089 A1 Feb. 1, 2018

Related U.S. Application Data

(63) Continuation of application No. 15/069,199, filed on Mar. 14, 2016, which is a continuation of application No. 13/881,447, filed as application No. PCT/SE2011/051335 on Nov. 8, 2011, now abandoned.

(60) Provisional application No. 61/410,957, filed on Nov. 8, 2010.

(30) Foreign Application Priority Data

Nov. 8, 2010 (SE) ...................................... 1051165

(51) Int. Cl.
A61K 31/55 (2006.01)
A61K 31/554 (2006.01)
A61K 31/575 (2006.01)
C07K 5/065 (2006.01)
A61K 38/05 (2006.01)
C07K 5/062 (2006.01)
A61K 38/00 (2006.01)

(52) U.S. Cl.
CPC .......... *C07K 5/06078* (2013.01); *A61K 31/55* (2013.01); *A61K 31/554* (2013.01); *A61K 31/575* (2013.01); *A61K 38/05* (2013.01); *C07K 5/0606* (2013.01); *C07K 5/06026* (2013.01); *A61K 38/00* (2013.01); *A61K 2121/00* (2013.01)

(58) Field of Classification Search
None
See application file for complete search history.

(56) References Cited

U.S. PATENT DOCUMENTS

| 3,539,380 | A | 11/1970 | Johnson |
|---|---|---|---|
| 4,172,120 | A | 10/1979 | Todd et al. |
| 4,507,235 | A | 3/1985 | Wunsch |
| 5,422,124 | A | 6/1995 | Valducci |
| 5,681,584 | A | 10/1997 | Savastano |
| 5,811,388 | A | 9/1998 | Friend et al. |
| 5,994,391 | A | 11/1999 | Lee et al. |
| 6,069,167 | A | 5/2000 | Sokol |
| 6,277,831 | B1 | 8/2001 | Frick et al. |
| 6,346,527 | B1 | 2/2002 | Takanaka et al. |
| 6,355,672 | B1 | 3/2002 | Yasuma et al. |
| 6,387,924 | B2 | 5/2002 | Lee et al. |
| 6,387,944 | B1 | 5/2002 | Frick et al. |
| 6,635,280 | B2 | 10/2003 | Shell et al. |
| 6,676,979 | B2 | 1/2004 | Marlett et al. |
| 6,906,058 | B2 | 6/2005 | Starke et al. |
| 6,943,189 | B2 | 9/2005 | Keller et al. |
| 7,019,023 | B2 | 3/2006 | Frick et al. |
| 7,125,864 | B2 | 10/2006 | Starke et al. |
| 7,132,416 | B2 | 11/2006 | Starke et al. |
| 7,132,557 | B2 | 11/2006 | Wilkes et al. |
| 7,192,945 | B2 | 3/2007 | Starke et al. |
| 7,192,946 | B2 | 3/2007 | Starke et al. |
| 7,192,947 | B2 | 3/2007 | Starke et al. |
| 7,226,943 | B2 | 6/2007 | Starke et al. |
| 7,238,684 | B2 | 7/2007 | Starke et al. |
| 7,514,421 | B2 | 4/2009 | Abrahamsson et al. |
| 8,067,584 | B2 | 11/2011 | Starke et al. |
| 9,023,368 | B2 | 5/2015 | Basit et al. |
| 9,409,875 | B2 | 8/2016 | Bohlin et al. |
| 9,684,018 | B2 | 6/2017 | Horanzy |
| 9,694,018 | B1* | 7/2017 | Gillberg .............. A61K 31/554 |
| 9,701,649 | B2 | 7/2017 | Bohlin et al. |
| 9,745,276 | B2 | 8/2017 | Bohlin et al. |
| 2002/0142054 | A1 | 10/2002 | Marlett et al. |
| 2003/0124088 | A1 | 7/2003 | Masuda et al. |
| 2003/0125316 | A1 | 7/2003 | Keller et al. |
| 2003/0143183 | A1 | 7/2003 | Knudsen et al. |
| 2003/0215843 | A1* | 11/2003 | Poupon ................ C12Q 1/6883 435/6.18 |
| 2004/0067933 | A1 | 4/2004 | Starke et al. |
| 2005/0009805 | A1 | 1/2005 | Sasahara et al. |
| 2005/0113362 | A1 | 5/2005 | Lindstedt et al. |
| 2005/0124557 | A1 | 6/2005 | Lindqvist |
| 2005/0171204 | A1 | 8/2005 | Lindstedt et al. |
| 2005/0197376 | A1 | 9/2005 | Kayakiri et al. |
| 2005/0266080 | A1 | 12/2005 | Desai et al. |
| 2005/0282822 | A1 | 12/2005 | Alstermark et al. |

(Continued)

FOREIGN PATENT DOCUMENTS

| CA | 2065151 | 3/1991 |
|---|---|---|
| DE | 3930168 | 3/1991 |

(Continued)

OTHER PUBLICATIONS

Hollands et al. (Journal of Pediatric Surgery, vol. 33, No. 2, Feb. 1998; pp. 220-224).*

(Continued)

*Primary Examiner* — Anna Pagonakis
(74) *Attorney, Agent, or Firm* — Fish & Richardson P.C.

(57) ABSTRACT

The present invention regards specific IBAT inhibitors useful in the prophylaxis and/or treatment of a liver disease. It also relates to compositions comprising these IBAT inhibitors, a method for treatment of the disorders and a kit comprising the substances or the compositions.

8 Claims, No Drawings

(56) References Cited

U.S. PATENT DOCUMENTS

| | | |
|---|---|---|
| 2006/0083790 A1 | 4/2006 | Anderberg et al. |
| 2006/0210633 A1 | 9/2006 | Dharmadhikari |
| 2007/0197522 A1 | 8/2007 | Edwards et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |

FOREIGN PATENT DOCUMENTS

| | | |
|---|---|---|
| DE | 19825804 | 8/2000 |
| EP | 0489423 | 12/1991 |
| EP | 0372542 | 10/1992 |
| EP | 0573848 | 5/1993 |
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1273307 | 1/2003 |
| EP | 1535913 | 6/2005 |
| EP | 1719768 | 11/2006 |
| GB | 2262888 | 7/1996 |
| JP | A-2004-516285 | 6/2004 |
| JP | B-3665055 | 6/2005 |
| JP | 2006/124695 | 5/2006 |
| JP | B-4870552 | 2/2012 |
| JP | A-2013-542953 | 11/2013 |
| JP | B-5421326 | 2/2014 |
| WO | WO 93/16055 | 8/1993 |
| WO | WO 94/00111 | 1/1994 |
| WO | WO 94/18183 | 8/1994 |
| WO | WO 94/18184 | 8/1994 |
| WO | WO 96/05188 | 2/1996 |
| WO | WO 96/08484 | 3/1996 |
| WO | WO 96/16051 | 5/1996 |
| WO | WO 97/33882 | 9/1997 |
| WO | WO 98/03818 | 1/1998 |
| WO | WO 98/07449 | 1/1998 |
| WO | WO 98/38182 | 9/1998 |
| WO | WO 98/40375 | 9/1998 |
| WO | WO 99/01149 | 1/1999 |
| WO | WO 99/32478 | 1/1999 |
| WO | WO 99/35135 | 7/1999 |
| WO | WO 99/64409 | 7/1999 |
| WO | WO 99/64410 | 12/1999 |
| WO | WO 00/01687 | 1/2000 |
| WO | WO 00/38725 | 7/2000 |
| WO | WO 00/38726 | 7/2000 |
| WO | WO 00/38727 | 7/2000 |
| WO | WO 00/38728 | 7/2000 |
| WO | WO 00/38729 | 7/2000 |
| WO | WO 00/47568 | 8/2000 |
| WO | WO 00/61568 | 10/2000 |
| WO | WO 00/62810 | 10/2000 |
| WO | WO 01/60807 | 8/2001 |
| WO | WO 01/66533 | 9/2001 |
| WO | WO 01/68096 | 9/2001 |
| WO | WO 01/68637 | 9/2001 |
| WO | WO 02/08211 | 1/2002 |
| WO | WO 02/09815 | 4/2002 |
| WO | WO 02/32428 | 4/2002 |
| WO | WO 02/50051 | 6/2002 |
| WO | WO 02/53548 | 6/2002 |
| WO | WO 03/020710 | 3/2003 |
| WO | WO 03/022286 | 3/2003 |
| WO | WO 03/022804 | 3/2003 |
| WO | WO 03/022825 | 3/2003 |
| WO | WO 03/022830 | 3/2003 |
| WO | WO 03/051821 | 6/2003 |
| WO | WO 03/051822 | 6/2003 |
| WO | WO 03/061663 | 7/2003 |
| WO | WO 03/091232 | 11/2003 |
| WO | WO 03/106482 | 11/2003 |
| WO | WO 04/006899 | 1/2004 |
| WO | WO 04/056748 | 7/2004 |
| WO | WO 04/076430 | 9/2004 |
| WO | WO 04/089350 | 9/2004 |
| WO | WO 04/020421 | 10/2004 |
| WO | WO2004/089350 | 10/2004 |
| WO | WO 07/009655 | 1/2007 |
| WO | WO 07/009656 | 1/2007 |
| WO | WO 08/058628 | 5/2008 |
| WO | WO 08/058630 | 5/2008 |
| WO | WO 08/058631 | 5/2008 |
| WO | WO 10/062861 | 6/2010 |
| WO | WO 2010/041268 | 9/2010 |
| WO | WO 11/137135 | 11/2011 |
| WO | WO 11/150286 | 12/2011 |
| WO | WO 12/064267 | 5/2012 |
| WO | WO 12/064268 | 5/2012 |
| WO | WO 13/063512 | 5/2013 |
| WO | WO 13/063526 | 5/2013 |
| WO | WO 2014/174066 | 10/2014 |
| WO | WO 2015/193788 | 12/2015 |

OTHER PUBLICATIONS

"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT02160782?term=LUM001&rank=7, 4 pages.

"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.

"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.

"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.

"An Extension Study to Evaluate the Long-Term Safety and Durability of Effect of LUM001 in the Treatment of Cholestatic Liver Disease in Subjects With Alagille Syndrome (IMAGINE-II)," Clinical Trials.gov, Apr. 16, 2014, retrieved on Oct. 3, 2014, http://clinicaltrials.gov/ct2/show/NCT02117713?term=LUM001&rank=2, 3 pages.

(56) References Cited

OTHER PUBLICATIONS

"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.

"EASL Clinical Practice Guidelines: Management of cholestatic liver diseases," European Assoc. for the Study of the Liver, Journal of Hepatology, 2009, 51:237-267.

"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.

"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.

"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.

"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.

"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.

"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.

"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.

"Progressive familial intrahepatic cholestasis," Wikipedia, the free encyclopedia, posted on or about Feb. 24, 2006, http://en.wikipedia.org/wiki/Progressive_familial_ intrahepatic_cholestasis, 3 pages.

"Safety and Efficacy Study of LUM001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.

"What is Alagille Syndrome?," European Medicines Agency, Jan. 21, 2014, retrieved on Oct. 3, 2014, http://www.ema.europa.eu/docs/en_GB/document_library/Orphan_designation/2014/01/WC500159874.pdf, 6 pages.

Alissa et al., "Invited Review: Update on Progressive Familial Intrahepatic Cholestasis," *Journal of Pediatric Gastroenterology and Nutrition*, 2008, 46:241-252.

American Diabetes Association, "Management of Dyslipidemia in Adults with Diabetes," Diabetes Care, Jan. 2003, 26(1).

Angulo, "Use of ursodeoxycholic acid in patients with liver disease," *Current Gastroenterology Reports*, Feb. 1, 2002, 4(1):37-44.

Artursson and Karlsson, "Corresalation Between Oral Drug Absorption in Humans and Apparent Drug Permeability Coefficients in Human Intestinal Epithelial (CACO-2) Cells," Biochemical and Biophysical Research Communications, Mar. 1991, 175(3):880-885.

Attili et al., "Bile Acid-induced Liver Toxicity: Relation to the Hydrophobic-Hydrophilic Balance of Bile Acids," Medical Hypotheses, 1986, 19:57-69.

Baghdasaryan et al., "Inhibition of intestinal bile acid absorption by ASBT inhibito A4250 protects against bile acid-mediated cholestatic liver injury in mice," J. Hepatology, 2014, 60:S57.

Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.

Bajor et al., "Bile acids: short and long term effects in the intestine," Scandanavian J. Gastro., 2010, 45:645-664.

Banker et al., "Modern Pharmaceutics, 3ed", Marcel Dekker, New York, 1996, pp. 451 and 596.

Bavin, "Polymorphism in Process Development," Chemistry and Industry, 527-529, 1989.

Board of Appeal of European Patent Office, Case No. T 077/08-3.3.01, dated May 24, 2011, 17 pages.

Bonge et al., "Cytostar-T Scintillating Microplate Assay for Measurement of Sodium-Dependent Bile Acid Uptake in Transfected HEK-293 Cells," Analytical Biochemistry, 2000, 282:94-101.

Brunzell and Hokanson, "Dislipidemia of Central Obesity and Insulin Resistance," Diabetes Care, 1999, 22(Suppl. 3):C10-C13.

Byrn et al., "Pharmaceutical Solids: A Strategic Approach to Regulatory Considerations," Pharmaceutical Research, 1995, 12(7), pp. 945-954.

Chen et al., "Inhibition of apical sodium-dependent bile acid transporter as a novel treatment for diabetes," Am J Physiol Endocrinol Metab, 2012, 302:E68-E76.

Chen et al., "Progressive Familial Intrahepatic Cholestasis, Type 1, Is Associated with Decreased Farnesoid X Receptor Activity," Gastroenterology, 2004, 126:756-764.

Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.

Chourasia et al., "Polysaccharides for colon targeted drug delivery," Drug Delivery, Academic Press, vol. 11, No. 2, Jan. 1, 2004, XP008060983.

Dashti et al., "A Phospholipidomic Analysis of All Defined Human Plasma Lipoproteins," Nature.com: Scientific Reports, Nov. 2011, DOI: 10.1038, 11 pages.

Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," *Hepatology: Autoimmune, Cholestatic and Biliary Disease*, May 2010, 1645-1655.

Davit-Spraul et al., "Progressive familial intrahepatic cholestasis," *Orphanet Journal of Rare Diseases*, Jan. 2009, 4:1-12.

Dawson et al., "Bile acid transporters" J. Lipid Res. 2009, 50, 2340-2357.

DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.

Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).

Dongiovanni et al., "Genetic Predisposition in NAFLD and NASH: Impact on Severity of Liver Disease and Response to Treatment," Curren Pharma Design, 2013, 19:5219-5238.

Espenshade and Hughes, "Regulation of Sterol Synthesis in Eukaryotes," Annu. Rev. Genet., 2007, 41:401-427.

Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.

Extended European Search Report in European Application No. 11840392.2, dated Feb. 24, 2014, 7 pages.

Extended European Search Report in European Application No. 11840481.3, dated Feb. 13, 2014, 10 pages.

(56) References Cited

OTHER PUBLICATIONS

Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.

Gillberg et al., "The IBAT Inhibition by A3309—A Potential Mechanism for the Treatment of Constipation," Gastroenterology, 2010, 138(5), Supp 1, S-224.

Glasgov et al., "Compensatory enlargement of human athersclerotic coronary arteries," N Engl. J. Med., May 1987, 316(22):1371-1375 (Abstract Only).

Govers et al., "Characterization of the adsorption of conjugated and unconjugated bile acids to insoluble, amorphous calcium phosphate", Journal of Lipid Research 35(5):741-748, 1994.

Hancock et al., "Molecular Mobility of amorphous pharmaceutical solids below their glass transition temperatures," 12(6): 799-806, 1995.

Heathcote, "Management of primary biliary cirrhosis," Hepatology, 2000, 31(4):1005-1013.

Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.

Huang et al., "Discovery of Potent, Nonsystemic Apical Sodium-Codependent Bile Acid Transporter Inhibitors (Part 2)," J. Med. Chem., 2005, 48:5853-5868.

International Preliminary Report on Patentability for International Application No. PCT/SE2011/051335, dated May 23, 2011, 7 pages.

International Preliminary Report on Patentability for International Application No. PCT/SE2011/051336, dated May 23, 2013, 11 pages.

International Search Report and Written Opinion for Application No. PCT/EP2014/058432, dated Jul. 11, 2014, 9 pages.

International Search Report and Written Opinion for International Application No. PCT/SE2011/051335, dated Feb. 3, 2012, 12pages.

International Search Report and Written Opinion for International Application No. PCT/SE2011/051336, dated Feb. 22, 2012, 18 pages.

Ishibashi et al., "Hypercholesterolemia in low density lipoprotein receptor knockout mice and its reversal by adenovirus-mediated gene delivery", Journal of Clinical Investigation 92(2):883-893, 1993.

Jacquet et al., "Alagille Syndrome in Adult Patients: It is Never Too Late," *American Journal of Kidney Diseases*, May 2007, 49(5):705-709.

Korman et al., "Assessment of Activity in Chronic Active Liver Disease," New England Journal of Medicine, 2010, 290(25):1399-1402.

Kumar and Tandon, "Use of ursodeoxycholic acid in liver diseases," J. Gastroenterology and Hepatology, 2001, 16:3-14.

Kurata et al., "A novel class of apical sodium-dependent bile acid transporter inhibitors: the amphiphilic 4-oxo-l-phenyl-1,4-dihydroquinoline derivatives," Bioorganic & Medicinal Chemistry Letters, 2004, 14:1183-1186.

Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.

Lewis et al., "Effects of 2164U90 on ileal bile acid adsorption and serum cholesterol in rats and mice", Journal of Lipid Research 36(5):1098-1105, 1995.

Ling, "Congenital cholestatic syndromes: What happens when children grow up?," Can J Gastroenterol, Nov. 11, 2007, 21(11):743-751.

Longo et al., "Hyperlipidemia in chronic cholestatic liver disease," Curr. Treat. Options Gastrenterol., 2001, 4:111-114.

Lykavieris et al., "Outcome of liver disease in children with Alagille syndrome: a study of 163 patients," *Gut*, 2001, 49:431-435.

MerckManuals com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.

Morissette et al., "High-throughput crystallization polymorphs, salts, co-crystals and solvates of pharmaceutical solids," Advanced Drug Delivery Reviews, 2004, 56:275-300.

Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.

Parker et al., "Molecular mechanisms underlying bile acid-stimulated glucagon-like peptide-1 secretion," British J. Pharmacology, 2012, 165:414-423.

Patani et al., "Bioisosterism: A Rational Approach in Drug Design," Chem Rev, 1996, 96:3147-3176.

Plump et al., "Severe hypercholesterolemia and atherosclerosis in apolipoprotein E-deficient mice created by homologous recombination in ES cells", Cell (71):343-353, 1992.

Podesta et al., "Treatment of pruritus of primary biliary cirrhosis with rifampin," Dig. Dis. Sci, 1991, 36(2):216-220.

Poupon et al., "Chronic Cholestatic Disease," J. Hepatology, 2000, 32(1):12-140.

Report filed at oral proceedings before opposition division, GMS-CFEP-2007-20, "Filtration and Drying Study on Amorphous and Form IV Atorvastatin Calcium," 2007.

Report EC20082069.02.01 dated Feb. 2009, filed with appellant's letter of Apr. 26, 2011.

Schiller, "Review article: the therapy of constipation", Alimentary Pharmacology and Therapeutics 15(6):749-763, 2001.

Shah et al., "Role of Caco-2 Cell Monolayers in Prediction of Intestinal Drug Absortption," . Biotechnol. Prog., 2006, 22:186-198.

Shang et al., "Colesevelam improves insulin resistance in a diet-induced obesity (F-DIO) rat model by increasing the release of GLP-1," Am J. Physiol Gastrointest Liver Physiol, 2010, 298:G419-G424.

Sorrentino et al., "A Clinical-Morphological Study on Cholestatic Presentation of Nonalcoholic Fatty Liver Disease," Digestive Disease and Sciences, Jun. 2005, 50(6):1130-1135.

Sprong et al., "Dietary Calcium Phosphate Promotes Listeria monosytogenes colonization and translocation in rats red diets containing corn oil but not milk fat1", J. Nutrition (US) 132(6):1269-1274, 2002.

Staels and Kuipers, "Bile Acid Sequestrants and the Treatment of Type 2 Diabetes Mellitus," Drugs, 2007, 67(10):1383-1392.

Stein, "Managing Dyslipidemia in the High-Risk Patient," Am J. Cardiol., 2002, 89:50-57.

Tanaka et al., "Genetic and Familial considerations of Primary Biliary Cirrhosis," Am. J. Gastroenterology, 2001, 96(1): 8-15.

Tollefson et al., "A novel class of apical sodium co-dependent bile acid transporter inhibitors: the 1,2-Benzothiazepines", Bioorganic and Medicinal Chemistry Letters 12:3727-3730, 2003.

Tremont et al., "Discovery of Potent, Nonsystemic Apical Sodium-Codependent Bile Acid Transporter Inhibitors (Part 1)," J. Med. Chem, 2005, 48:5837-5852.

Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.

Van Tilberg et al., "Na+-dependent bile acid transport in the ileum: the balance between diarrhea and constipation", Gastroenterology 98(1):25-32, 1989.

Vippagunta et al., "Crystalline solids", Advanced Drug Delivery Reviews 48:3-26, 2001.

Watts and Illum, "Colonic Drug Delivery," Drug Development and Industrial Pharmacy, 1997, 23(9):893-913.

Welberg et al., "Calcium and the prevention of colon cancer", Scandinavian J. Gasteroenterology Suppl. 188:52-59, 1991.

Williams et al., Foye's Principles of Medicinal Chemistry, 5th Edition, 2002, 59-63.

(56) References Cited

OTHER PUBLICATIONS

Wolff, "Burger's Medicinal Chemistry, 5ed, Part I", John Wiley & Sons, 1995, pp. 975-977.
Das & Kar., Non alcoholic steatohepatitis. JAPI. 53:, Mar. 2005.
Berazs et al., Nor-ursodeoxycholic acid reverses hepatocyte-specific nemo-dependnt steatohepatitis. Gut, 2011: 60: 387-396.
Carulli et al, "Review article: effect of bile salt pool composition on hepatic and biliary functions," Aliment. Pharmacol. Ther. 2000, vol. 14, suppl. 2, p. 14-18.
Islam and Di Baise, "Bile Acids: An underrecognized and underappreciated cause of chronic diarrhea," Pract. Gastroenterol. 2012, vol. 36(10), p. 32-44.
Jacobsen et al., "Effect of enterocoated cholestyramine on bowel habit after ileal resection: a double blind crossover study," Br. Med. J. 1985, vol. 290, p. 1315-1318.
Marzorati et al, "A novel hypromellose capsule, with acid resistance properties, permits the targeted delivery of acid-sensitive products to the intestine, " LWT-Food Sci. Techno.1 2015, vol. 60, p. 544-551.
Pattni and Walters, "Recent advances in the understanding of bile acid malabsorption," Br. Med. Bull. 2009, vol. 92, p. 79-93.
Possemiers et al, "PCR-DGGE-based quantification of stability of the microbial community in a simulator of the human intestinal microbial ecosystem," FEMS Microbiol. Ecol. 2004, vol. 49, p. 495-507.
Sinha and Kumria, "Microbially triggered drug delivery to the colon," Eur. J. Pharm. Sci. 2003, vol. 18, p. 3-18.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
International Search Report and Written Opinion for Application No. PCT/SE2017/050128, dated May 8, 2017, 16 pages.
International Search Report and Written Opinion for Application No. PCT/SE2017/050126, dated Apr. 24, 2017, 27 pages.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan. 10, 2013), 102(1), pp. 83-89.
International Search Report, Application No. , dated Sep. 15, 2015.
Alonso et al., "Histologic pathology of the liver in progressive familial intrahepatic cholestasis," Journal of Pediatric Gastroenterology and Nutrition, 14: 128-133, 1994.
Billington et al., "Effects of bile salts on the plasma membranes of isolated rat hepatocytes," Bichem. J. 188: 321-327, 1980.
Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.
Chen et al., "Bile salt export pump is dysregulated with altered farnesoid X receptor isoform expression in patients with hepatocelular carcinoma," Hepatologu, 57: 4, 1530-1541, 2013.
Chen et al., "Serum and urine metabolite profiling reveals potential biomarkers of human hepatocellular carcinoma," Molecular and Cellular Proteomics 10.7, 2011.
Faubion et al., "Toxic bile salts induce rodent hepatocyte apoptosis via direct activation of Fas," The Journal of Clinical Investigation, 103: 1, 137-145, 1999.
Jansen et al., "Endogenous bile acids as carcinogens," Journal of Hepatology, 47, 434-435, 2007.
Knisely et al., "Hepatocellular Carcinoma in ten children under five years of age with bile salt export pump deficiency," Hepatology, 44: 2, 478-486, 2006.
Kurbegov et al., Biliary diversion for progressive familial intrahepatic cholestasis: Improved liver morphology and bile acid profile, Gastroenterology, 125: 4, 1227-1234, 2003.
Perez et al., "Bile-acid-induced cell injury and protection," World J Gastroenterol, 15: 25, 1677-1689, 2009.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Rolo et al., "Bile acids affect liver mitochondrial bioenergetics: Possible relevance for cholestasis therapy," Toxocological Sciences, 57: 177-185, 2000.
Wang et al., "Bile acid receptors and liver cancer," Curr. Pathobiol Rep, 1, 29-35, 2013.
Whitington et al., "Partial external diversion of bile for the treatment of intractable pruitus associated with intrahepatic cholestasis," Gastroenterology, 95: 1, 130-136, 1988 (Abstract only).
Woolbright et al., "Novel insight into mechanisms of cholestatic liver injury," World Journal of Gastroenterology, 18: 36, 4985-4993, 2012.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zhang et al., Abcb11 deficiency induces cholestasis coupled to impaired B-Fatty acid oxidation in mice, Journal of biological chemistry, 287: 29, 24784-2479, 2012.
Zhang et al., "Effect of bile duct ligation on bile acid composition in mouse serum and liver," Liver int, 32: 1, 58-69, 2012.
U.S. Appl. No. 15/726,203, filed Oct. 5, 2017, Gillberg et al.
Alvarez, Fernando; "Treatments in chronic cholestasis in children." Ann. Nestlé (2008) 66 p. 127-135.
Balbach et al.. "Pharmaceutical evaluation of early development candidates "the 100 mg-approach"," Int J Pharm, May 4, 2004, 275(1):1-12.
Caira, "Crystalline Polymorphism of Organic Compounds," in: Topics in Current Chemistry, Jan. 1998, 198:163-208.
Forner et al., "Treatment of hepatocellular carcinoma," Critical Reviews in Oncology/Hematology, 2006, 60:89-98.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Search Report and Written Opinion for Application No. PCT/SE2017/050127, dated May 8, 2017, 16 pages.
International Search Report and Written Opinion for International Application No. PCT/EP2015/074573, dated Apr. 28, 2016, 11 pages.
Singhal et al., "Drug polymorphism and dosage form design: a practical perspective," Adv Drug Deliv Rev, Feb. 23, 2004, 56(3):335-347.
The ileal bile acid transport inhibitor A4250 decreases pruritus and serum bile acids in cholestatic liver diseases—an ongoing multiple dose, open-label, multicenter study, 2017 (Abstract only).
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Brunt et al., "Nonalcoholic Steatohepatitis: A Proposal for Grading and Staging the Histological Lesions," American Jounral of Gastroenterology, Sep. 1999, 94(9): 2467-2474.
Ekkehard Sturm et al. The ileal bile acid transport inhibitor A4250 reduced pruritus and serum bile acid levels in children with cholestatic liver disease and pruritus: final results from a multiple-dose, open-label, multinational study Hepatology 2017; 66: 646-47 (Suppl. 1). doi: 10.1002/hep.29501.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
hepc.liverfoundation.org' [online]. "Nonalcoholic Fatty Liver Disease," Brochure, 2016 [retrieved on Feb. 1, 2018]. Retrived from the Internet: URL<http://hepc.liverfoundation.org/wp-content/uploads/2012/07/NAFLD-Brochure-2016.pdf>, 8 pages.

(56) References Cited

OTHER PUBLICATIONS

Jiang et al., "Non alcoholic steatohepatitis a precursor for hepatocellular carcinoma development," World Journal of Gastroenterology: WJG, Nov. 28, 2014, 20(44):16464-16473.
Mouzaki and Allard, "Non-alcoholic steatohepatitis: the therapeutic challenge of a global epidemic," Annals of Gastroenterology, 2012, 25: 207-217.
Perumpail et al., "Clinical epidemiology and disease burden of nonalcoholic fatty liver disease," World Journal of Gastroenterology, Dec. 2017, 23(47): 8263-8276.
Satapathy and Sanyal, "Epidemiology and Natural History of Non-alcoholic Fatty Liver Disease," Seminars in Liver Disease, Aug. 2015, 35(3): 221-235.
Scheuer, "Primary Biliary Cirrhosis," Proc. R. Soc. Med., Dec. 1967, 60:1257-1260.
Sun et al., "Bile acids promote diethylnitrosamine-induced hepatocellular carcinoma via increased inflammatory signaling," American Journal of Physiology-Gastrointestinal and Liver Physiology, May 5, 2016, 311(1):G91-104.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Xie et al., "Dysregulated hepatic bile acids collaboratively promote liver carcinogenesis," Int J Cancer, Oct. 15, 2016, 139(8):1764-1775.
U.S. Appl. No. 13/881,435, filed May 22, 2013, Gillberg et al.
U.S. Appl. No. 14/505,811, filed Oct. 3, 2014, Gillberg et al.
U.S. Appl. No. 15/230,124, filed Aug. 5, 2016, Gillberg et al.
U.S. Appl. No. 13/881,447, filed May 17, 2013, Gillberg et al.
U.S. Appl. No. 14/505,782, filed Oct. 3, 2014, Gillberg et al.
U.S. Appl. No. 15/069,355, filed Mar. 14, 2016, Gillberg et al.
U.S. Appl. No. 15/069,199, filed Mar. 14, 2016, Gillberg et al.
U.S. Appl. No. 15/276,446, filed Sep. 26, 2016, Gillberg et al.
U.S. Appl. No. 15/726,071, filed Oct. 5, 2017, Gillberg et al.
U.S. Appl. No. 15/722,110, filed Oct. 2, 2017, Gillberg et al.
U.S. Appl. No. 15/894,472, filed Feb. 12, 2018, Gillberg et al.
U.S. Appl. No. 15/134,583, filed Apr. 21, 2016, Bohlin et al.
U.S. Appl. No. 15/134,586, filed Apr. 21, 2016, Bohlin et al.
U.S. Appl. No. 15/449,645, filed Mar. 3, 2017, Gillberg et al.
U.S. Appl. No. 15/449,781, filed Mar. 3, 2017, Gillberg et al.
U.S. Appl. No. 15/449,779, filed Mar. 3, 2017, Gillberg et al.
U.S. Appl. No. 15/519,808, filed Apr. 17, 2017, Ymen et al.
U.S. Appl. No. 15/320,651, filed Dec. 20, 2016, Ando et al.
U.S. Appl. No. 15/320,621, filed Dec. 20, 2016, Ando et al.

\* cited by examiner

IBAT INHIBITORS FOR THE TREATMENT OF LIVER DISEASES

CROSS-REFERENCE TO RELATED APPLICATIONS

This application is a continuation of U.S. patent application Ser. No. 15/069,199, filed Mar. 14, 2016, which is a continuation of U.S. patent application Ser. No. 13/881,447, filed May 17, 2013, which is a National Stage application under 35 U.S.C. § 371 of International Application No. PCT/SE2011/051335, filed Nov. 8, 2011, which claims the benefit of U.S. Patent Application No. 61/410,957, filed Nov. 8, 2010, and Swedish Patent Application No. 1051165-7, filed Nov. 8, 2010, all of which are incorporated by reference in their entirety.

BACKGROUND OF THE INVENTION

Ileal bile acid transporter (IBAT) is the main mechanism for re-absorption of bile acids from the GI tract. Partial or full blockade of that mechanism will result in lower concentration of bile acids in the small bowel wall, portal vein, liver parenchyma, intrahepatic biliary tree, extrahepatic biliary tree, including gall bladder.

Diseases which may benefit from partial or full blockade of the IBAT mechanism may be those either having as a primary pathophysiological defect, causing or having symptoms of too high concentration of bile acids in serum and in the above organs. WO 2008/058630 describes the effect of certain ileal bile acid transport (IBAT) in the treatment of liver disease related to fat disorders.

SUMMARY OF THE INVENTION

The present invention regards specific IBAT inhibitors in the prophylaxis and/or treatment of a liver disease.

DETAILED DESCRIPTION OF THE INVENTION

The invention relates to IBAT inhibitory compounds of formula (I):

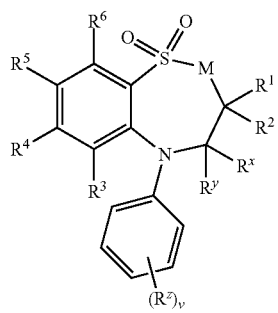

(I)

wherein:
M is $CH_2$, NH
One of $R^1$ and $R^2$ are selected from hydrogen or $C_{1-6}$alkyl and the other is selected from $C_{1-6}$alkyl;
$R^x$ and $R^y$ are independently selected from hydrogen, hydroxy, amino, mercapto, $C_{1-6}$alkyl, $C_{1-6}$alkoxy, N—($C_{1-6}$alkyl)amino, N,N—($C_{1-6}$alkyl)$_2$amino, $C_{1-6}$alkylS(O)$_a$ wherein a is 0 to 2

$R^z$ is selected from halo, nitro, cyano, hydroxy, amino, carboxy, carbamoyl, mercapto, sulphamoyl, $C_{1-6}$alkyl, $C_{2-6}$alkenyl, $C_{2-6}$alkynyl, $C_{1-6}$alkanoyl, $C_{1-6}$alkanoyloxy, N—($C_{1-6}$alkyl)amino, N,N—($C_{1-6}$alkyl)$_2$amino, $C_{1-6}$alkanoylamino, N—($C_{1-6}$alkyl)carbamoyl, N,N—($C_{1-6}$alkyl)$_2$carbamoyl, $C_{1-6}$alkylS(O)$_a$ wherein a is 0 to 2, $C_{1-6}$alkoxycarbonyl, N—($C_{1-6}$alkyl)sulphamoyl and N,N—($C_{1-6}$alkyl)$_2$sulphamoyl;
v is 0-5;
one of $R^4$ and $R^5$ is a group of formula (IA):

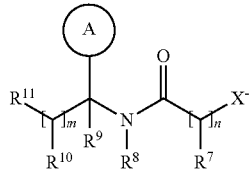

(IA)

$R^3$ and $R^6$ and the other of $R^4$ and $R^5$ are independently selected from hydrogen, halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^3$ and $R^6$ and the other of $R^4$ and $R^5$ may be optionally substituted on carbon by one or more $R^{16}$;
X is —O—, —N($R^a$)—, —S(O)$_b$— or —CH($R^a$)—; wherein $R^a$ is hydrogen or $C_{1-6}$alkyl and b is 0-2;
Ring A is aryl or heteroaryl; wherein Ring A is optionally substituted by one or more substituents selected from $R^{17}$;
$R^7$ is hydrogen, $C_{1-4}$alkyl, carbocyclyl or heterocyclyl; wherein $R^7$ is optionally substituted by one or more substituents selected from $R^{18}$;
$R^8$ is hydrogen or $C_{1-4}$alkyl;
$R^9$ is hydrogen or $C_{1-4}$alkyl;
$R^{10}$ is hydrogen, $C_{1-4}$alkyl, carbocyclyl or heterocyclyl; wherein $R^{10}$ is optionally substituted by one or more substituents selected from $R^{19}$;
$R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein $R^c$ and $R^d$ are independently selected from $C_{1-6}$alkyl; or $R^{11}$ is a group of formula (IB) or (IC):

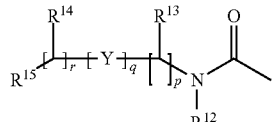

(IB)

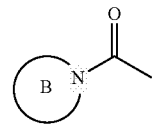

(IC)

wherein:
Y is —N(R$^n$)—, —N(R$^n$)C(O)—, —N(R$^n$)C(O)(CR$^s$R$^t$)$_x$N(R$^n$)C(O)—, —O—, and —S(O)a-; wherein a is 0-2, v is 1-2, $R^s$ and $R^t$ are independently selected from hydrogen or $C_{1-4}$alkyl optionally substituted by $R^{26}$ and $R^n$ is hydrogen or $C_{1-4}$alkyl;

$R^{12}$ is hydrogen or $C_{1-4}$alkyl;

$R^{13}$ and $R^{14}$ are independently selected from hydrogen, $C_{1-4}$alkyl, carbocyclyl or heterocyclyl; and when q is 0, $R^{14}$ may additionally be selected from hydroxy wherein $R^{13}$ and $R^{14}$ may be independently optionally substituted by one or more substituents selected from $R^{20}$;

$R^{15}$ is carboxy, sulpho, sulphino, phosphono, —P(O)(OR$^e$)(OR$^f$), —P(O)(OH)(OR$^e$), —P(O)(OH)(R$^e$) or —P(O)(OR$^e$)(R$^f$) wherein $R^e$ and $R^f$ are independently selected from $C_{1-6}$alkyl;

p is 1-3; wherein the values of $R^{13}$ may be the same or different;

q is 0-1;

r is 0-3; wherein the values of $R^{14}$ may be the same or different;

m is 0-2; wherein the values of $R^{10}$ may be the same or different;

n is 1-3; wherein the values of $R^7$ may be the same or different;

Ring B is a nitrogen linked heterocyclyl substituted on carbon by one group selected from $R^{23}$, and optionally additionally substituted on carbon by one or more $R^{24}$; and wherein if said nitrogen linked heterocyclyl contains an —NH— moiety, that nitrogen may be optionally substituted by a group selected from $R^{25}$;

$R^{16}$, $R^{17}$ and $R^{18}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl and N,N—($C_{1-4}$alkyl)$_2$sulphamoyl; wherein $R^{16}$, $R^{17}$ and $R^{18}$ may be independently optionally substituted on carbon by one or more $R^{21}$;

$R^{19}$, $R^{20}$, $R^{24}$ and $R^{26}$ are independently selected from halo, nitro, cyano, hydroxy, amino, carboxy, carbamoyl, mercapto, sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N—($C_{1-4}$alkyl)amino, N,N—($C_{1-4}$alkyl)$_2$amino, $C_{1-4}$alkanoylamino, N—($C_{1-4}$alkyl)carbamoyl, N,N—($C_{1-4}$alkyl)$_2$carbamoyl, $C_{1-4}$alkylS(O)$_a$ wherein a is 0 to 2, $C_{1-4}$alkoxycarbonyl, N—($C_{1-4}$alkyl)sulphamoyl, N,N—($C_{1-4}$alkyl)$_2$sulphamoyl, carbocyclyl, heterocyclyl, benzyloxycarbonylamino, sulpho, sulphino, amidino, phosphono, —P(O)(OR$^a$)(OR$^b$), —P(O)(OH)(OR$^a$), —P(O)(OH)(R$^a$) or —P(O)(OR$^a$)(R$^b$), wherein $R^a$ and $R^b$ are independently selected from $C_{1-6}$alkyl; wherein $R^{19}$, $R^{20}$, $R^{24}$ and $R^{26}$ may be independently optionally substituted on carbon by one or more $R^{22}$;

$R^{21}$ and $R^{22}$ are independently selected from halo, hydroxy, cyano, carbamoyl, ureido, amino, nitro, carboxy, carbamoyl, mercapto, sulphamoyl, trifluoromethyl, trifluoromethoxy, methyl, ethyl, methoxy, ethoxy, vinyl, allyl, ethynyl, methoxycarbonyl, formyl, acetyl, formamido, acetylamino, acetoxy, methylamino, dimethylamino, N-methylcarbamoyl, N,N-dimethylcarbamoyl, methylthio, methylsulphinyl, mesyl, N-methylsulphamoyl and N,N-dimethylsulphamoyl;

$R^{23}$ is carboxy, sulpho, sulphino, phosphono, —P(O)(OR$^g$)(OR$^h$), —P(O)(OH)(OR$^g$), —P(O)(OH)(R$^g$) or —P(O)(OR$^g$)(R$^h$) wherein $R^g$ and $R^h$ are independently selected from $C_{1-6}$alkyl;

$R^{25}$ is selected from $C_{1-6}$alkyl, $C_{1-6}$alkanoyl, $C_{1-6}$alkylsulphonyl, $C_{1-6}$alkoxycarbonyl, carbamoyl, N—($C_{1-6}$alkyl)carbamoyl, N,N—($C_{1-6}$alkyl)carbamoyl, benzyl, benzyloxycarbonyl, benzoyl and phenylsulphonyl;

or a pharmaceutically acceptable salt, solvate, solvate of such a salt or a prodrug thereof for use in the prophylaxis or treatment of a liver disease.

Compounds as used in accordance with the invention improve liver tests (serum amino transferases) and liver histology and significantly reduce hydroxyproline content and the number of infiltrating neutrophils and proliferating hepatocytes and cholangiocytes.

In the literature IBAT inhibitors are often referred to by different names. It is to be understood that where IBAT inhibitors are referred to herein, this term also encompasses compounds known in the literature as: i) ileal apical sodium co-dependent bile acid transporter (ASBT) inhibitors; ii) bile acid transporter (BAT) inhibitors; iii) ileal sodium/bile acid cotransporter system inhibitors; iv) apical sodium-bile acid cotransporter inhibitors; v) ileal sodium-dependent bile acid transport inhibitors; vi) bile acid reabsorption (BARI's) inhibitors; and vii) sodium bile acid transporter (SBAT) inhibitors; where they act by inhibition of IBAT.

In this specification the term "alkyl" includes both straight and branched chain alkyl groups but references to individual alkyl groups such as "propyl" are specific for the straight chain version only. For example, "$C_{1-6}$alkyl" includes $C_{1-4}$alkyl, $C_{1-3}$alkyl, propyl, isopropyl and t-butyl. However, references to individual alkyl groups such as 'propyl' are specific for the straight chained version only and references to individual branched chain alkyl groups such as 'isopropyl' are specific for the branched chain version only. A similar convention applies to other radicals, for example "phenyl$C_{1-6}$alkyl" would include phenyl$C_{1-4}$alkyl, benzyl, 1-phenylethyl and 2-phenylethyl. The term "halo" refers to fluoro, chloro, bromo and iodo.

Where optional substituents are chosen from "one or more" groups it is to be understood that this definition includes all substituents being chosen from one of the specified groups or the substituents being chosen from two or more of the specified groups.

"Heteroaryl" is a totally unsaturated, mono or bicyclic ring containing 3-12 atoms of which at least one atom is chosen from nitrogen, sulphur or oxygen, which may, unless otherwise specified, be carbon or nitrogen linked. Preferably "heteroaryl" refers to a totally unsaturated, monocyclic ring containing 5 or 6 atoms or a bicyclic ring containing 9 or 10 atoms of which at least one atom is chosen from nitrogen, sulphur or oxygen, which may, unless otherwise specified, be carbon or nitrogen linked. In another aspect of the invention, "heteroaryl" refers to a totally unsaturated, monocyclic ring containing 5 or 6 atoms or a bicyclic ring containing 8, 9 or 10 atoms of which at least one atom is chosen from nitrogen, sulphur or oxygen, which may, unless otherwise specified, be carbon or nitrogen linked. Examples and suitable values of the term "heteroaryl" are thienyl, isoxazolyl, imidazolyl, pyrrolyl, thiadiazolyl, isothiazolyl, triazolyl, pyranyl, indolyl, pyrimidyl, pyrazinyl, pyridazinyl, pyridyl and quinolyl. Preferably the term "heteroaryl" refers to thienyl or indolyl.

"Aryl" is a totally unsaturated, mono or bicyclic carbon ring that contains 3-12 atoms. Preferably "aryl" is a monocyclic ring containing 5 or 6 atoms or a bicyclic ring containing 9 or 10 atoms. Suitable values for "aryl" include phenyl or naphthyl. Particularly "aryl" is phenyl.

A "heterocyclyl" is a saturated, partially saturated or unsaturated, mono or bicyclic ring containing 3-12 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form the S-oxides. Preferably a "heterocyclyl" is a saturated, partially saturated or unsaturated, mono or bicyclic ring containing 5 or 6 atoms of which at least one atom is chosen from nitrogen, sulphur or oxygen, which may, unless otherwise specified, be carbon or nitrogen linked, wherein a —$CH_2$— group can optionally be replaced by a —C(O)— or a ring sulphur atom may be optionally oxidised to form S-oxide(s). Examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydrothienyl, 2,4-dioxoimidazolidinyl, 2-oxo-1,3,4-(4-triazolinyl), 2-oxazolidinonyl, 5,6-dihydrouracilyl, 1,3-benzodioxolyl, 1,2,4-oxadiazolyl, 2-azabicyclo [2.2.1] heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

A "carbocyclyl" is a saturated, partially saturated or unsaturated, mono or bicyclic carbon ring that contains 3-12 atoms; wherein a —$CH_2$— group can optionally be replaced by a —C(O)—. Preferably "carbocyclyl" is a monocyclic ring containing 5 or 6 atoms or a bicyclic ring containing 9 or 10 atoms. Suitable values for "carbocyclyl" include cyclopropyl, cyclobutyl, 1-oxocyclopentyl, cyclopentyl, cyclopentenyl, cyclohexyl, cyclohexenyl, phenyl, naphthyl, tetralinyl, indanyl or 1-oxoindanyl. Particularly "carbocyclyl" is cyclopropyl, cyclobutyl, 1-oxocyclopentyl, cyclopentyl, cyclopentenyl, cyclohexyl, cyclohexenyl, phenyl or 1-oxoindanyl.

An example of "$C_{1-6}$alkanoyloxy" and "$C_{1-4}$alkanoyloxy" is acetoxy. Examples of "$C_{1-6}$alkoxycarbonyl" and "$C_{1-4}$ alkoxycarbonyl" include methoxycarbonyl, ethoxycarbonyl, n- and t-butoxycarbonyl. Examples of "$C_{1-6}$alkoxy" and "$C_{1-4}$alkoxy" include methoxy, ethoxy and propoxy. Examples of "$C_{1-6}$alkanoylamino" and "$C_{1-4}$alkanoylamino" include formamido, acetamido and propionylamino. Examples of "$C_{1-6}$alkylS(O)$_a$ wherein a is 0 to 2" and "$C_{1-4}$alkylS(O)$_a$ wherein a is 0 to 2" include methylthio, ethylthio, methylsulphinyl, ethylsulphinyl, mesyl and ethylsulphonyl. Examples of "$C_{1-6}$alkanoyl" and "$C_{1-4}$alkanoyl" include $C_{1-3}$alkanoyl, propionyl and acetyl. Examples of "N—($C_{1-6}$alkyl)amino" and "N—($C_{1-4}$alkyl)amino" include methylamino and ethylamino. Examples of "N,N—($C_{1-6}$alkyl)$_2$amino" and "N,N—($C_{1-4}$alkyl)$_2$amino" include di-N-methylamino, di-(N-ethyl)amino and N-ethyl-N-methyl-amino. Examples of "$C_{2-6}$alkenyl" and "$C_{2-4}$alkenyl" are vinyl, allyl and 1-propenyl. Examples of "$C_{2-6}$ alkynyl" and "$C_{2-4}$alkynyl" are ethynyl, 1-propynyl and 2-propynyl. Examples of "N—($C_{1-6}$alkyl)sulphamoyl" and "N—($C_{1-4}$alkyl)sulphamoyl" are N—($C_{1-3}$alkyl)sulphamoyl, N-(methyl)sulphamoyl and N-(ethyl)sulphamoyl. Examples of "N—($C_{1-6}$alkyl)$_2$sulphamoyl" and "N-4alkyl)$_2$sulphamoyl" are N,N-(dimethyl)sulphamoyl and N-(methyl)-N-(ethyl)sulphamoyl. Examples of "N—($C_{1-6}$alkyl)carbamoyl" and "N—($C_{1-4}$alkyl)carbamoyl" are methylaminocarbonyl and ethylaminocarbonyl. Examples of "N,N—($C_{1-6}$alkyl)$_2$carbamoyl" and "N,N—($C_{1-4}$alkyl)$_2$-carbamoyl" are dimethylaminocarbonyl and methylethylaminocarbonyl. Examples of "$C_{1-6}$ alkoxycarbonylamino" are ethoxycarbonylamino and t-butoxycarbonylamino. Examples of "N'—($C_{1-6}$alkyl)ureido" are N'-methylureido and N'-ethylureido. Examples of "N—($C_{1-6}$alkyl)ureido are N-methylureido and N-ethylureido. Examples of "N',N'—($C_{1-6}$alkyl)$_2$ureido are N',N'-dimethylureido and N'-methyl-N'-ethylureido. Examples of "N'—($C_{1-6}$alkyl)-N—($C_{1-6}$alkyl)ureido are N'-methyl-N-methylureido and N'-propyl-N-methylureido. Examples of "N',N'—($C_{1-6}$alkyl)$_2$-N—($C_{1-6}$alkyl)ureido are N',N'-dimethyl-N-methylureido and N'-methyl-N'-ethyl-N-propylureido.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulphuric, phosphoric, trifluoroacetic, citric or maleic acid.

In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl) amine.

Compounds of formula (I) may be administered in the form of a pro-drug which is broken down in the human or animal body to give a compound of the formula (I). Examples of pro-drugs include in vivo hydrolysable esters and in vivo hydrolysable amides of a compound of the formula (I).

An in vivo hydrolysable ester of a compound of the formula (I) containing carboxy or hydroxy group is, for example, a pharmaceutically acceptable ester which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$ alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

A suitable value for an in vivo hydrolysable amide of a compound of the formula (I) containing a carboxy group is, for example, a N—$C_{1-6}$alkyl or N,N-di-$C_{1-6}$alkyl amide such as N-methyl, N-ethyl, N-propyl, N,N-dimethyl, N-ethyl-N-methyl or N,N-diethyl amide.

It is also to be understood that certain compounds of the formula (I) can exist in solvated as well as unsolvated forms such as, for example, hydrated forms. It is to be understood that the invention encompasses all such solvated forms which possess IBAT inhibitory activity.

Preferred values of $R^1$, $R^2$, $R^3$, $R^4$, $R^5$ and $R^6$ are as follows. Such values may be used where appropriate with any of the definitions, claims or embodiments defined hereinbefore or hereinafter.

Preferably $R^1$ and $R^2$ are independently selected from $C_{1-4}$alkyl.

More preferably $R^1$ and $R^2$ are independently selected from ethyl or butyl.

More preferably $R^1$ and $R^2$ are independently selected from ethyl, propyl or butyl.

In one aspect of the invention particularly $R^1$ and $R^2$ are both butyl.

In a further aspect of the invention particularly $R^1$ and $R^2$ are both propyl.

In another aspect of the invention particularly one of $R^1$ and $R^2$ is ethyl and the other is butyl.

Preferably $R^x$ and $R^y$ are independently selected from hydrogen or $C_{1-6}$alkyl.

More preferably $R^x$ and $R^y$ are both hydrogen.

Preferably $R^z$ is selected from halo, amino, $C_{1-6}$alkyl, $C_{1-6}$alkoxycarbonylamino or N'—($C_{1-6}$alkyl)ureido.

More preferably $R^z$ is selected from chloro, amino, t-butyl, t-butoxycarbonylamino or N'-(t-butyl)ureido.

Preferably v is 0 or 1.

In one aspect of the invention, more preferably v is 0.

In one aspect of the invention, more preferably v is 1.

In one aspect of the invention preferably $R^4$ is a group of formula (IA) (as depicted above).

In another aspect of the invention preferably $R^5$ is a group of formula (IA) (as depicted above).

Preferably $R^3$ and $R^6$ are hydrogen.

Preferably the other of $R^4$ and $R^5$ that is not the group of formula (IA) is selected from halo, $C_{1-4}$alkoxy or $C_{1-4}$alkylS$(O)_a$ wherein a is 0 to 2; wherein that $R^4$ or $R^5$ may be optionally substituted on carbon by one or more $R^{16}$; wherein $R^{16}$ is independently selected from hydroxy and N,N—($C_{1-4}$alkyl)$_2$amino.

More preferably the other of $R^4$ and $R^5$ that is not the group of formula (IA) is selected from bromo, methoxy, isopropoxy, methylthio, ethylthio, isopropylthio or mesyl; wherein that $R^4$ or $R^5$ may be optionally substituted on carbon by one or more $R^{16}$; wherein $R^{16}$ is independently selected from hydroxy and N,N-dimethylamino.

Particularly the other of $R^4$ and $R^5$ that is not the group of formula (IA) is selected from bromo, methoxy, isopropoxy, methylthio, ethylthio, isopropylthio, 2-hydroxyethylthio, 2-(N,N-dimethylamino) ethylthio or mesyl.

More particularly the other of $R^4$ and $R^5$ that is not the group of formula (IA) is methylthio. Preferably the other of $R^4$ and $R^5$ that is not the group of formula (IA) is selected from hydrogen, halo, $C_{1-4}$alkoxy or $C_{1-4}$alkylS$(O)_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)$_2$amino.

More preferably the other of $R^4$ and $R^5$ that is not the group of formula (IA) is selected from hydrogen, bromo, methoxy, isopropoxy, methylthio, ethylthio, isopropylthio or mesyl; wherein that $R^4$ or $R^5$ may be optionally substituted on carbon by one or more $R^{16}$; wherein $R^{16}$ is independently selected from hydroxy, carboxy and N,N-dimethylamino.

Particularly the other of $R^4$ and $R^5$ that is not the group of formula (IA) is selected from hydrogen, bromo, methoxy, isopropoxy, methylthio, carboxymethylthio, ethylthio, isopropylthio, 2-hydroxyethylthio, 2-(N,N-dimethylamino) ethylthio or mesyl.

In another aspect of the invention, more preferably the other of $R^4$ and $R^5$ that is not the group of formula (IA) is selected from hydrogen, chloro, bromo, methoxy, isopropoxy, methylthio, ethylthio or isopropylthio; wherein that $R^4$ or $R^5$ may be optionally substituted on carbon by one or more $R^{16}$; wherein $R^{16}$ is independently selected from hydroxy, carboxy and N,N-dimethylamino.

In another aspect of the invention, particularly the other of $R^4$ and $R^5$ that is not the group of formula (IA) is selected from hydrogen, chloro, bromo, methoxy, isopropoxy, methylthio, carboxymethylthio, ethylthio, isopropylthio, 2-hydroxyethylthio or 2-(N,N-dimethylamino) ethylthio.

In another aspect of the invention, more particularly the other of $R^4$ and $R^5$ that is not the group of formula (IA) is bromo or chloro.

In another aspect of the invention, more particularly the other of $R^4$ and $R^5$ that is not the group of formula (IA) is methoxy.

In one aspect of the invention, preferably Ring A is aryl.

In another aspect of the invention, preferably Ring A is heteroaryl.

When Ring A is aryl, preferably Ring A is phenyl.

When Ring A is heteroaryl, preferably Ring A is thienyl or indolyl.

Preferably Ring A is aryl or heteroaryl; wherein Ring A is optionally substituted by one or more substituents selected from $R^{17}$; wherein $R^{17}$ is selected from halo, hydroxy or $C_{1-4}$alkyl; wherein $R^{17}$ may be optionally substituted on carbon by one or more $R^{21}$; wherein $R^{21}$ is selected from halo.

Preferably X is —O.

More preferably Ring A is phenyl, thienyl or indolyl; wherein Ring A is optionally substituted by one or more substituents selected from halo, hydroxy or trifluoromethyl.

Particularly Ring A is selected from phenyl, 4-hydroxyphenyl, thien-2-yl, 4-trifluoromethylphenyl, 3-hydroxyphenyl, 2-fluorophenyl, 2,3-dihydroxyphenyl or indol-3-yl.

More particularly Ring A is phenyl.

In another aspect of the invention, preferably Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo.

In another aspect of the invention, more preferably Ring A is phenyl, thienyl or indolyl; wherein Ring A is optionally substituted by one or more substituents selected from halo, hydroxy, methoxy or trifluoromethyl.

In another aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 2,3-dihydroxyphenyl or indol-3-yl.

In a further aspect of the invention, particularly Ring A is selected from phenyl, 4-hydroxyphenyl, 4-methoxyphenyl, thien-2-yl, 4-trifluoromethylphenyl, 3-hydroxyphenyl, 2-fluorophenyl, 4-fluorophenyl, 2,3-dihydroxyphenyl or indol-3-yl.

Preferably $R^7$ is hydrogen, $C_{1-4}$alkyl or carbocyclyl.

More preferably $R^7$ is hydrogen, methyl or phenyl.

Particularly $R^7$ is hydrogen.

In one aspect of the invention, preferably $R^8$ is hydrogen.

In another aspect of the invention, preferably $R^8$ is $C_{1-4}$alkyl.

In another aspect of the invention, more preferably $R^8$ is hydrogen or methyl.

In one aspect of the invention, preferably $R^9$ is hydrogen.

In another aspect of the invention, preferably $R^9$ is $C_{1-4}$alkyl.

In another aspect of the invention, more preferably $R^9$ is hydrogen or methyl.

Preferably $R^{10}$ is hydrogen.

In one aspect of the invention, preferably $R^{11}$ is carboxy, sulpho, sulphino, phosphono, —P(O)(OR$^c$)(OR$^d$), —P(O)(OH)(OR$^c$), —P(O)(OH)(R$^d$) or —P(O)(OR$^c$)(R$^d$) wherein R$^c$ and R$^d$ are independently selected from $C_{1-6}$alkyl.

In another aspect of the invention, preferably $R^{11}$ is a group of formula (IB) (as depicted above).

Preferably $R^{11}$ is carboxy, —P(O)(OH)(OR$^c$) or a group of formula (IB) (as depicted above).

More preferably $R^{11}$ is carboxy, —P(O)(OH)(OEt) or a group of formula (IB) (as depicted above).

In another aspect of the invention, preferably $R^{11}$ is carboxy, sulpho, —P(O)(OH)(OR$^c$) wherein R$^c$ is selected from $C_{1-4}$alkyl or a group of formula (IB) (as depicted above).

Preferably Y is —NH— or —NHC(O)—.

More preferably Y is —NHC(O)—.

In one aspect of the invention, preferably $R^{12}$ is hydrogen.

In another aspect of the invention, preferably $R^{12}$ is $C_{1-4}$alkyl.

In another aspect of the invention, more preferably $R^{12}$ is hydrogen or methyl.

Preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy.

More preferably $R^{13}$ is hydrogen, methyl or phenyl; wherein $R^{13}$ is optionally substituted by one or more substituents selected from $R^{20}$; wherein $R^{20}$ is hydroxy.

Particularly $R^{13}$ is hydrogen, hydroxymethyl or phenyl.

More particularly $R^{13}$ is hydrogen or hydroxymethyl.

In another aspect of the invention, preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy, carboxy, carbocyclyl or amino; wherein $R^{20}$ may be optionally substituted on carbon by one or more $R^{22}$; $R^{22}$ is hydroxy.

In another aspect of the invention, more preferably $R^{13}$ is hydrogen, methyl, ethyl, butyl or phenyl; wherein $R^{13}$ is optionally substituted by one or more substituents selected from $R^{20}$; wherein $R^{20}$ is hydroxy, carboxy, phenyl or amino; wherein $R^{20}$ may be optionally substituted on carbon by one or more $R^{22}$; $R^{22}$ is hydroxy.

In another aspect of the invention, particularly $R^{13}$ is hydrogen, hydroxymethyl, 4-aminobutyl, 2-carboxyethyl, 4-hydroxybenzyl or phenyl.

In a further aspect of the invention, preferably $R^{13}$ is hydrogen, $C_{1-4}$alkyl or carbocyclyl; wherein $R^{13}$ is optionally substituted by one or more substituents selected from $R^{20}$; wherein $R^{20}$ is hydroxy, carboxy, carbocyclyl, heterocyclyl or amino; wherein $R^{20}$ may be optionally substituted on carbon by one or more $R^{22}$; $R^{22}$ is hydroxy.

In a further aspect of the invention, more preferably $R^{13}$ is hydrogen, methyl, ethyl, butyl or phenyl; wherein $R^{13}$ is optionally substituted by one or more substituents selected from $R^{20}$; wherein $R^{20}$ is hydroxy, carboxy, phenyl, imidazolyl or amino; wherein $R^{20}$ may be optionally substituted on carbon by one or more $R^{22}$; $R^{22}$ is hydroxy.

In a further aspect of the invention, particularly $R^{13}$ is hydrogen, hydroxymethyl, 4-aminobutyl, 2-carboxyethyl, 4-hydroxybenzyl, imidazol-5-ylmethyl or phenyl.

In another further aspect of the invention, preferably $R^{13}$ is hydrogen, $C_{1-4}$alkyl, carbocyclyl or $R^{23}$; wherein $R^{13}$ is optionally substituted by one or more substituents selected from $R^{20}$; wherein $R^{20}$ is hydroxy, $C_{1-4}$alkylS(O)a wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy.

In another further aspect of the invention, more preferably $R^{13}$ is hydrogen, methyl, ethyl, butyl or phenyl or $R^{23}$; wherein $R^{13}$ is optionally substituted by one or more substituents selected from $R^{20}$; wherein $R^{20}$ is hydroxy, methylthio, methoxy, amino, imidazolyl or mercapto; wherein $R^{20}$ may be independently optionally substituted on carbon by one or more $R^{22}$; $R^{22}$ is selected from hydroxy; and $R^{23}$ is carboxy.

In another further aspect of the invention, particularly $R^{13}$ is hydrogen, carboxy, hydroxymethyl, mercaptomethyl, methoxymethyl, methylthiomethyl, 2-methylthioethyl, 4-aminobutyl, 4-hydroxybenzyl, imidazol-5-ylmethyl or phenyl.

In another aspect more particularly $R^{13}$ is methylthiomethyl, methylsulphinylmethyl or methylsulphonylmethyl.

Preferably $R^{14}$ is hydrogen.

In another aspect of the invention, preferably $R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy.

In another aspect of the invention, more preferably $R^{14}$ is selected from hydrogen, methyl or phenyl; wherein said methyl or phenyl may be optionally substituted by one or more substituents selected from $R^{20}$; and $R^{20}$ is hydroxy.

In another aspect of the invention, particularly $R^{14}$ is hydrogen, phenyl or hydroxymethyl.

Particularly $R^{15}$ is carboxy or sulpho.

In one aspect of the invention, more particularly $R^{15}$ is carboxy.

In another aspect of the invention, more particularly $R^{15}$ is sulpho.

Preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl.

More preferably $R^{15}$ is carboxy, sulpho, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl.

Preferably $R^{15}$ is carboxy, sulpho, —P(O)(OEt)(OEt), —P(O)(OH)(OEt), —P(O)(OH)(Me) or —P(O)(OEt)(Me).

Preferably $R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl or $R^{15}$ is a group of formula (IC) (as depicted above).

More preferably $R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted above).

Preferably $R^{15}$ is carboxy, sulpho, phosphono, —P(O)(OEt)(OEt), —P(O)(Ot-Bu)(Ot-Bu), —P(O)(OH)(OEt), —P(O)(OH)(Me) or —P(O)(OEt)(Me) or $R^{15}$ is a group of formula (IC) (as depicted above).

In one aspect of the invention, preferably $R^{15}$ is carboxy.

In another aspect of the invention, preferably $R^{15}$ is sulpho.

In another aspect of the invention, preferably $R^{15}$ is —P(O)(OH)(OEt).

In another aspect of the invention, preferably $R^{15}$ is —P(O)(OH)(Me).

In another aspect of the invention, preferably $R^{15}$ is —P(O)(OEt)(Me).

In one aspect of the invention, preferably $R^{24}$ is hydrogen.

In another aspect of the invention, preferably $R^{24}$ is $C_{1-4}$alkyl.

Preferably $R^{25}$ is hydrogen.

Preferably $R^{26}$ is carboxy.

Preferably p is 1 or 2; wherein the values of $R^{13}$ may be the same or different.

In one aspect of the invention, more preferably p is 1.

In another aspect of the invention, more preferably p is 2; wherein the values of $R^{13}$ may be the same or different.

In a further aspect of the invention, more preferably p is 3; wherein the values of $R^{13}$ may be the same or different.

In one aspect of the invention, preferably q is 0.

In a further aspect of the invention, preferably q is 1.

In one aspect of the invention, preferably r is 0.

In one aspect of the invention, more preferably r is 1.

In another aspect of the invention, more preferably r is 2; wherein the values of $R^{14}$ may be the same or different.

In a further aspect of the invention, more preferably r is 3; wherein the values of $R^{14}$ may be the same or different.

Preferably m is 0.

In another aspect of the invention, preferably m is 0 or 1.

Preferably n is 1.

In another aspect of the invention, preferably n is 1 or 2.

Preferably z is 1.

The group of formula (IA) wherein $R^7$ is hydrogen, methyl or phenyl, n is 1, Ring A is phenyl, thienyl or indolyl; wherein Ring A is optionally substituted by one or more substituents selected from halo, hydroxy or trifluoromethyl, m is 0 and $R^9$ is carboxy, —P(O)(OH)(OR$^e$) or a group of formula (IB).

The group of formula (IA) wherein: X is -O-.

Ring A is phenyl, thienyl or indolyl; wherein Ring A is optionally substituted by one or more substituents selected from halo, hydroxy, methoxy or trifluoromethyl;
$R^7$ is hydrogen, methyl or phenyl;
$R^8$ is hydrogen or methyl;
$R^9$ is hydrogen or methyl;
$R^{10}$ is hydrogen;
m is 0-2 wherein the values of $R^{10}$ may be the same or different; and $R^{11}$ is carboxy, —P(O)(OH)(OEt) or a group of formula (IB) (as depicted in claim 1); The group of formula (IB) wherein $R^{10}$ is hydrogen, hydroxymethyl or phenyl, p is 1 or 2; wherein the values of $R^{10}$ may be the same or different and $R^{11}$ is carboxy or sulpho.

The group of formula (IB) wherein:
$R^{12}$ is hydrogen or methyl;
$R^{13}$ is hydrogen, methyl, ethyl, butyl or phenyl or $R^{23}$; wherein $R^{13}$ is optionally substituted by one or more substituents selected from $R^{20}$; $R^{20}$ is hydroxy, methylthio, methoxy, amino, imidazolyl or mercapto; wherein $R^{20}$ may be independently optionally substituted on carbon by one or more hydroxy; $R^{23}$ is carboxy; Y is —NH— or —NHC(O)—; $R^{14}$ is selected from hydrogen, methyl or phenyl; wherein said methyl or phenyl may be optionally substituted by one or more substituents selected from hydroxy; $R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from methyl or ethyl or $R^{15}$ is a group of formula (IC) (as depicted in claim 1);
p is 1-3 wherein the values of $R^{13}$ may be the same or different;
q is 0-1; and
r is 0-3 wherein the values of $R^{14}$ may be the same or different;

The group of formula (IC) wherein
$R^{24}$ is hydrogen;
$R^{25}$ is hydrogen;
$R^{26}$ is carboxy; and
z is 1;
or a pharmaceutically acceptable salt, solvate, solvate of such a salt or a prodrug thereof.

Therefore in a further aspect of the invention, there is provided a compound of formula (I) as depicted above wherein:
$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—(C$_{1-4}$alkyl)$_2$amino;
$R^5$ is a group of formula (IA);
Ring A is aryl or heteroaryl; wherein Ring A is optionally substituted by one or more substituents selected from $R^{17}$; wherein
$R^{17}$ is selected from halo, hydroxy or $C_{1-4}$alkyl; wherein $R^{17}$ may be optionally substituted on carbon by one or more $R^{21}$; wherein
$R^{21}$ is selected from halo;
$R^7$ is hydrogen, $C_{1-4}$alkyl or carbocyclyl;
$R^{11}$ is carboxy, —P(O)(OH)(OR$^e$) or a group of formula (IB) (as depicted above);
$R^{13}$ is hydrogen, $C_{1-4}$alkyl or carbocyclyl; wherein $R^{13}$ is optionally substituted by one or more substituents selected from $R^{20}$; wherein
$R^{20}$ is hydroxy;
$R^{15}$ is carboxy or sulpho;
p is 1 or 2; wherein the values of $R^{13}$ may be the same or different;
m is 0; and
n is 1;
or a pharmaceutically acceptable salt, solvate, solvate of such a salt or a prodrug thereof.

Therefore in an additional aspect of the invention, there is provided a compound of formula (I) as depicted above wherein:
$R^1$ and $R^2$ are both butyl or one of $R^1$ and $R^2$ is ethyl and the other is butyl;
$R^4$ is methylthio;
$R^5$ is a group of formula (IA) (as depicted above);
$R^3$ and $R^6$ are hydrogen;
Ring A is phenyl;
$R^7$ is hydrogen;
$R^{11}$ is a group of formula (IB) (as depicted above);
$R^{13}$ is hydrogen or hydroxymethyl;
$R^{15}$ is carboxy or sulpho;
p is 1 or 2; wherein the values of $R^{13}$ may be the same or different;
m is 0;
n is 1;
or a pharmaceutically acceptable salt, solvate, solvate of such a salt or a prodrug thereof.

Therefore in an additional further aspect of the invention, there is provided a compound of formula (I) as depicted above wherein:
$R^1$ and $R^2$ are independently selected from ethyl or butyl;
$R^3$ and $R^6$ are hydrogen;
$R^4$ is selected from halo, $C_{1-4}$alkoxy or $C_{1-4}$alkylS(O)$_a$ wherein a is 0 to 2; wherein that $R^4$ may be optionally substituted on carbon by one or more $R^{16}$; wherein $R^{16}$ is independently selected from hydroxy and N,N—($C_{1-4}$alkyl)$_2$amino;
$R^5$ is a group of formula (IA);
Ring A is aryl or heteroaryl; wherein Ring A is optionally substituted by one or more substituents selected from $R^{17}$;
$R^7$ is hydrogen, $C_{1-4}$alkyl or carbocyclyl;
$R^8$ is hydrogen or methyl;
$R^9$ is hydrogen or methyl;
$R^{11}$ is carboxy, —P(O)(OH)(OR$^c$) or a group of formula (IB) (as depicted above);
X is —NH— or —NHC(O)—;
$R^{12}$ is hydrogen or methyl;
$R^{13}$ is hydrogen, $C_{1-4}$alkyl or carbocyclyl; wherein $R^{13}$ is optionally substituted by one or more substituents selected from $R^{20}$;
$R^{14}$ is hydrogen;
$R^{15}$ is carboxy or sulpho;
$R^{17}$ is selected from halo, hydroxy, $C_{1-4}$alkyl or $C_{1-4}$alkoxy; wherein $R^{17}$ may be optionally substituted on carbon by one or more $R^{21}$;
$R^{20}$ is hydroxy, carboxy, carbocyclyl or amino; wherein $R^{20}$ may be optionally substituted on carbon by one or more $R^{22}$;
$R^{21}$ is selected from halo;
$R^{22}$ is hydroxy;
p is 1-3; wherein the values of $R^{13}$ may be the same or different.
q is 0-1;
r is 0-3; wherein the values of $R^{14}$ may be the same or different; and wherein if q is 1, r is not 0;
m is 0-2; and
n is 1-3;
or a pharmaceutically acceptable salt, solvate, solvate of such a salt or a prodrug thereof.

Therefore in another additional further aspect of the invention, there is provided a compound of formula (I) as depicted above wherein:
$R^1$ and $R^2$ are independently selected from $C_{1-4}$alkyl;
$R^x$ and $R^y$ are both hydrogen;
$R^z$ is selected from halo, amino, $C_{1-6}$alkyl, $C_{1-6}$alkoxycarbonylamino or N'—($C_{1-6}$alkyl)ureido;
v is 0 or 1;
$R^3$ and $R^6$ are hydrogen;
one of $R^4$ and $R^5$ is a group of formula (IA) (as depicted above) and the other is selected from hydrogen, halo, $C_{1-4}$alkoxy or $C_{1-4}$alkylS(O)$_a$ wherein a is 0 to 2; wherein that $R^4$ or $R^5$ may be optionally substituted on carbon by one or more $R^{16}$; wherein $R^{16}$ is independently selected from hydroxy, carboxy and N,N—($C_{1-4}$alkyl)2amino;
X is -0-;
$R^7$ is hydrogen, methyl or phenyl;
$R^8$ is hydrogen or methyl;
Ring A is aryl or heteroaryl; wherein Ring A is optionally substituted by one or more substituents selected from $R^{17}$; wherein $R^{17}$ is selected from halo, hydroxy, $C_{1-4}$alkyl or $C_{1-4}$alkoxy; wherein $R^{17}$ may be optionally substituted on carbon by one or more $R^{21}$; wherein $R^{21}$ is selected from halo;
$R^9$ is hydrogen or methyl;
$R^{10}$ is hydrogen;
$R^{11}$ is carboxy, —P(O)(OH)(OR$^c$) wherein R$^c$ is selected from $C_{1-4}$alkyl or a group of formula (IB) (as depicted above);
$R^{12}$ is hydrogen or methyl;
Y is —NH— or —NHC(O)—;
$R^{13}$ is hydrogen, $C_{1-4}$alkyl, carbocyclyl or $R^{23}$; wherein $R^{13}$ is optionally substituted by one or more substituents selected from $R^{20}$; wherein $R^{20}$ is hydroxy, $C_{1-4}$alkylS(O)$_a$ wherein a is 0, $C_{1-4}$alkoxy, amino, carbocyclyl, heterocyclyl or mercapto; wherein $R^{20}$ may be independently optionally substituted on carbon by one or more $R^{22}$; $R^{22}$ is selected from hydroxy; and $R^{23}$ is carboxy;
$R^{14}$ is selected from hydrogen, $C_{1-4}$alkyl or carbocyclyl; wherein said $C_{1-4}$alkyl or carbocyclyl may be optionally substituted by one or more substituents selected from $R^{20}$; and $R^{20}$ is hydroxy;
$R^{15}$ is carboxy, sulpho, phosphono, —P(O)(OR$^e$)(OR$^f$), —P(O)(OH)(OR$^e$), —P(O)(OH)(R$^e$) or —P(O)(OR$^e$)(R$^f$) wherein R$^e$ and R$^f$ are independently selected from $C_{1-4}$alkyl or $R^{15}$ is a group of formula (IC) (as depicted above);
$R^{24}$ is hydrogen;
$R^{25}$ is hydrogen;
$R^{26}$ is carboxy;
p is 1-3; wherein the values of $R^{13}$ may be the same or different;
q is 0-1;
r is 0-3; wherein the values of $R^{14}$ may be the same or different;
m is 0-2; wherein the values of $R^{10}$ may be the same or different;
n is 1-2; wherein the values of $R^7$ may be the same or different;
z is 0-1; wherein the values of $R^{25}$ may be the same or different;
or a pharmaceutically acceptable salt, solvate, solvate of such a salt or a prodrug thereof.

In another aspect of the invention, preferred compounds of the invention are any one of the Examples or a pharmaceutically acceptable salt, solvate, solvate of such a salt or a prodrug thereof.

In another aspect of the invention, preferred compounds of the invention are any one of the Examples or a pharmaceutically acceptable salt, solvate, solvate of such a salt or a prodrug thereof.

An aspect of the invention is a compound of formula II

Formula II

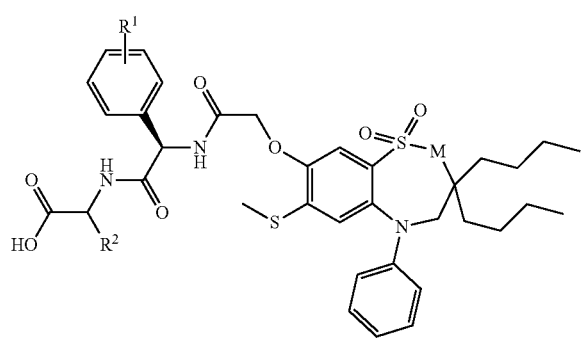

wherein
M is CH$_2$ or NH;
$R^1$ is H or hydroxy;

R² is H, CH₃, —CH₂CH₃, —CH₂CH₂CH₃, —CH₂CH₂CH₂CH₃, —CH(CH₃)₂, —CH₂CH(CH₃)₂, —CH(CH₃)CH₂CH₃, —CH₂OH, —CH₂OCH₃, —CH(OH)CH₃, —CH₂SCH₃, or —CH₂CH₂SCH₃;
for use in the prophylaxis or treatment of a liver disease.

Examples of useful substances in accordance with the invention are:

1,1-Dioxo-3,3-dibutyl-5-phenyl-7-methylthio-8-(N—{(R)-α-[N-(carboxymethyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N'—((S)-1-carboxyethyl)carbamoyl]benzyl}carbamoylmethoxy)-2,3,4,5-tetrahydro-1,5-benzothiazepine, 1,1-Dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N'—((S)-1-carboxypropyl)carbamoyl]-4-hydroxybenzyl}carbamoylmethoxy)-2,3,4,5-tetrahydro-1,5-benzothiazepine, 1,1-Dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine, 1,1-Dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine and 1,1-dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine.

Compounds of formula (I) or formula (II) may have chiral centres and/or geometric isomeric centres (E- and Z-isomers), and it is to be understood that the invention encompasses all such optical, diastereoisomers and geometric isomers that possess IBAT inhibitory activity. The invention relates to any and all tautomeric forms of the compounds of the formula (I) or formula (II) that possess IBAT inhibitory activity.

The invention also relates all possible isomers of the compounds of the invention such as, optical and/or geometrical, pure or as a mixture, in all proportions, of the said compounds of formulas I and II and those specifically mentioned and the possible tautomeric forms In certain embodiments, compounds described herein have one or more chiral centres. As such, all stereoisomers are envisioned herein. In various embodiments, compounds described herein are present in optically active or racemic forms. It is to be understood that the compounds of the present invention encompasses racemic, optically-active, regioisomeric and stereoisomeric forms, or combinations thereof that possess the therapeutically useful properties described herein. Preparation of optically active forms is achieve in any suitable manner, including by way of non-limiting example, by resolution of the racemic form by recrystallization techniques, by synthesis from optically-active starting materials, by chiral synthesis, or by chromatographic separation using a chiral stationary phase. In some embodiments, mixtures of one or more isomer are utilized as the therapeutic compound described herein. In certain embodiments, compounds described herein, contains one or more chiral centres. These compounds are prepared by any means, including enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, chromatography, and the like.

The compounds may exist in free-acid or free-base form, or in a pharmaceutically acceptable salt form. In certain embodiments, a compound described herein exists in an unsolvated or solvated form, wherein solvated forms comprise any pharmaceutically acceptable solvent, e.g., water, ethanol, and the like.

The invention further regards a composition comprising at least one IBAT inhibitor of Formula (I) or Formula (II), for use in the prophylaxis and/or treatment of a liver disease.

An aspect of the invention is the use of a compound of Formula (I) or Formula (II), for the preparation of a medicine for the treatment of a liver disease.

An IBAT inhibitor of Formula I or Formula II) may be used together with at least one other therapeutically active compound as described herein, in the preparation of a medicament for the prophylactic and/or therapeutic treatment of a liver disease.

Liver Diseases

Liver disease is herein defined as any Bile Acid (BA) dependent disease in the liver and in organs connected therewith, such as the pancreas portal vein, the liver parenchyma, the intrahepatic biliary tree, the extrahepatic biliary tree, and the gall bladder.

Ileal bile acid transporter (IBAT) is the main mechanism for re-absorption of bile acids from the GI tract. Partial or full blockade of that mechanism will result in lower concentration of bile acids in the small bowel wall, the portal vein, the liver parenchyma, the intrahepatic biliary tree, the extrahepatic biliary tree, and in the gall bladder. Diseases which may benefit from partial or full blockade of the IBAT mechanism may be those having a primary pathophysiological defect, causing or having symptoms of too high concentration of bile acids in serum and in the above organs.

An aspect of the invention is a compound of Formula (I) or Formula (II) as defined above, for use in the prophylaxis or treatment of liver parenchyma; an Inherited metabolic disorder of the liver; Byler syndrome; a primary defect of bile acid (BA) synthesis such as cerebrotendinous, or xanthomatosis; a secondary defect such as Zellweger's syndrome, neonatal hepatitis, cystic fibrosis, manifestations in the liver, ALGS (Alagilles syndrome), PFIC (progressive familial intrahepatic cholestasis, autoimmune hepatitis, primary biliary cirrhosis (PBC), liver fibrosis, non alcoholic fatty liver disease, NAFLD/NASH, portal hypertension, general cholestasis such as in jaundice due to drugs or during pregnancy, intra and extrahepatic cholestasis such as hereditary forms of cholestasis such as PFIC1, Primary sclerosing cholangitis, gall stones and choledocholithiasis, malignancy causing obstruction of the biliary tree, symptoms (scratching, pruritus) due to cholestasis/jaundice, pancreatitis, chronic autoimmune liver disease leading to progressive cholestasis, or pruritus of cholestatic liver disease.

An aspect of the invention is a compound of Formula (I) or Formula (II) as defined above, for use in the prophylaxis or treatment of a hepatic disorder or a hepatic related condition, fatty liver, hepatic steatosis, non-alcoholic steatohepatitis (NASH), alcoholic hepatitis, acute fatty liver, fatty liver of pregnancy, drug-induced hepatitis, iron overload disorders, hepatic fibrosis, hepatic cirrhosis, hepatoma, viral hepatitis and problems in relation to tumours and neoplasmas of the liver, of the biliary tract and of the pancreas.

Combination with Other Active Substances

An aspect of the invention is an IBAT inhibitor according to formula (I) or Formula (II) as defined above, in combination with at least one other therapeutically active substance. The at least one other therapeutically active substance may be an IBAT inhibitor compound.

Incretines and Hormones Produced by the L Cells

The at least one other therapeutically active substance may be an Incretine or a hormone produced by the L cells.

In an aspect of the invention, the at least one other therapeutically active substance is a L-cell endocrine peptide enhancer such as a GLP-1 enhancer. Examples of a GLP-1 enhancer useful in accordance with the invention are GLP-1, a GLP-1 secretion enhancer, a GLP-1 degradation inhibitor, or a combination thereof.

In an aspect of the invention, the L-cell endocrine peptide enhancer is a GLP-2 enhancer such as a GLP-2, a GLP-2 secretion enhancer, a GLP-2 degradation inhibitor, or a combination thereof.

In an aspect of the invention the L-cell endocrine peptide enhancer is a PYY enhancer such as an oxyntomodulin enhancer.

Incretin Mimetics

In an aspect of the invention, the at least one other therapeutically active substance is an incretin mimetic such as exenatide (Byetta®).

One aspect of the invention is an oral combination of an IBAT inhibitor of Formula (I) or Formula (II) as disclosed herein and a DPP-IV inhibitor.

Enteroendocrine Peptides

In an aspect of the invention, the at least one other therapeutically active substance is an enteroendocrine peptide such as GLP-1 or GLP-1 analogs, for example Taspoglutide® (Ipsen), or the like.

Combination Therapy with an IBAT Inhibitor and a DPP-IV Inhibitor

In an aspect of the invention, the at least one other therapeutically active substance is a DPP-IV inhibitor.

One aspect of the invention is a combination of an IBAT-inhibitor and metformin and/or sitagliptin (Janumet®) and/or DPP-IV inhibitors suitable for use with the methods described herein include but are not limited to (2S)-1-{2-[(3-hydroxy-1-adamantyl)amino]-acetyl}pyrrolidine-2-carbonitrile (vildagliptin), (3R)-3-amino-1-[9-(trifluoromethyl)-1,4,7,8-tetrazabicyclo[4.3.0]nona-6,8-dien-4-yl]-4-(2,4,5-trifluorophenyl)butan-1-one (sitagliptin), (1S,3S,5S)-2-[(2S)-2-amino-2-(3-hydroxy-1-adamantyl)acetyl]-2-azabicyclo[-3.1.0]hexane-3-carbonitrile (saxagliptin), and 2-({6-[(3R)-3-aminopiperidin-1-yl]-3-methyl-2,4-dioxo-3,4-dihydropyrimidi-n-1(2H)-yl}methyl)benzonitrile (alogliptin).

TGR5 Receptor Modulators

In one aspect of the invention, the at least one other therapeutically active substance is a TGR5 agonist. TGR5 modulators (e.g. agonists) include, but are not limited to, the compounds described in WO 2008/091540, WO 2008/067219 and U.S. Appl. No. 2008/0221161.

Thiazolidinediones

In one embodiment of the invention, the at least one other therapeutically active substance is a thiazolidinedione such as Rosiglitazone (Avandia), Pioglitazone (Actos), Troglitazone (Rezulin), MCC-555, rivoglitazone, ciglitazone or the like.

Combination Therapy with an IBAT INHIBITOR, a Biliary Shunt and a DPP-IV Inhibitor In one embodiment of the invention, an IBAT INHIBITOR of Formula (I) or Formula (II) as described herein, is administered in combination with a DPP-IV inhibitor and/or a biliary shunt. Examples of biliary shunts include but are not limited to shunts described in WO 2007/0050628, which disclosure is incorporated herein by reference.

As used herein, the term "additive effect" describes the combined effect of two (or more) pharmaceutically active agents that is equal to the sum of the effect of each agent given alone. A synergistic effect is one in which the combined effect of two (or more) pharmaceutically active agents is greater than the sum of the effect of each agent given alone. Any suitable combination of an ASBTI with one or more of the aforementioned other active ingredients and optionally with one or more other pharmacologically active substances is contemplated as being within the scope of the methods described herein.

In some embodiments, the particular choice of compounds depends upon the diagnosis of the attending physicians and their judgment of the condition of the individual and the appropriate treatment protocol. The compounds are optionally administered concurrently (e.g., simultaneously, essentially simultaneously or within the same treatment protocol) or sequentially, depending upon the nature of the disease, disorder, or condition, the condition of the individual, and the actual choice of compounds used. In certain instances, the determination of the order of administration, and the number of repetitions of administration of each therapeutic agent during a treatment protocol, is based on an evaluation of the disease being treated and the condition of the individual.

In some embodiments, therapeutically-effective dosages vary when the drugs are used in treatment combinations. Methods for experimentally determining therapeutically-effective dosages of drugs and other agents for use in combination treatment regimens are described in the literature.

In some embodiments of the combination therapies described herein, dosages of the co-administered compounds vary depending on the type of co-drug employed, on the specific drug employed, on the disease or condition being treated and so forth. In addition, when co-administered with one or more biologically active agents, the compound provided herein is optionally administered either simultaneously with the biologically active agent(s), or sequentially. In certain instances, if administered sequentially, the attending physician will decide on the appropriate sequence of therapeutic compound described herein in combination with the additional therapeutic agent.

The multiple therapeutic agents (at least one of which is a therapeutic compound described herein) are optionally administered in any order or even simultaneously. If simultaneously, the multiple therapeutic agents are optionally provided in a single, unified form, or in multiple forms (by way of example only, either as a single pill or as two separate pills). In certain instances, one of the therapeutic agents is optionally given in multiple doses. In other instances, both are optionally given as multiple doses. If not simultaneous, the timing between the multiple doses is any suitable timing, e.g., from more than zero weeks to less than four weeks. In addition, the combination methods, compositions and formulations are not to be limited to the use of only two agents; the use of multiple therapeutic combinations are also envisioned (including two or more compounds described herein).

In certain embodiments, a dosage regimen to treat, prevent, or ameliorate the condition(s) for which relief is sought, is modified in accordance with a variety of factors. These factors include the disorder from which the subject suffers, as well as the age, weight, sex, diet, and medical condition of the subject. Thus, in various embodiments, the dosage regimen actually employed varies and deviates from the dosage regimens set forth herein.

In some embodiments, the pharmaceutical agents which make up the combination therapy described herein are provided in a combined dosage form or in separate dosage forms intended for substantially simultaneous administration. In certain embodiments, the pharmaceutical agents that make up the combination therapy are administered sequentially, with either therapeutic compound being administered by a regimen calling for two-step administration. In some embodiments, two-step administration regimen calls for sequential administration of the active agents or spaced-apart administration of the separate active agents. In certain embodiments, the time period between the multiple administration steps varies, by way of non-limiting example, from a few minutes to several hours, depending upon the properties of each pharmaceutical agent, such as potency, solubility, bioavailability, plasma half-life and kinetic profile of the pharmaceutical agent.

The invention also regards IBAT inhibitor compounds described herein in combination with at least one bile acid binder e.g. a resin such as cholestyramine, cholestipol and colesevelam.

Bile Acid Binders (Bile Acid Sequestrants, Resins)

In one embodiment of the invention, an IBAT inhibitor of formula (I) or Formula (II) as defined above, may be administered as a pharmaceutical formulation also comprising at least one bile acid binder, said formulation being designed to deliver the bile acid binder in the colon and the IBAT inhibitor in the small intestine.

Examples of useful bile acid binders according to the invention are Cholestyramine, which is a hydrophilic polyacrylic quaternary ammonium anion exchange resin, known to be effective in reducing blood cholesterol levels. Cholestyramine, and various compositions including cholestyramine, are described, for example, in British Pat Nos. 929,391 and 1,286,949; and U.S. Pat. Nos. 3,383,281; 3,308,020; 3,769,399; 3,846,541; 3,974,272; 4,172,120; 4,252,790; 4,340,585; 4,814,354; 4,874,744; 4,895,723; 5,695,749; and 6,066,336. Cholestyramine is commercially available from Novopharm, USA Inc (Questrans Light), Upsher-Smith (PREVALITE (D), and Apothecon. As used herein, "cholestyramine" includes any such composition comprising cholestyramine, or pharmaceutically acceptable salts thereof. These are also called Questrans™ Questran Light Questrans Light (cholestyramine) is a non-absorbable anion binding resin FDA approved for the treatment of hypercholesterolemia.

An amine polymer having a first substituent, bound to a first amine of the amine polymer, that includes a hydrophobic aliphatic moiety, and a second substituent, bound to a second amine of the amine polymer, that includes an aliphatic quaternary amine-containing moiety as described in U.S. Pat. Nos. 5,693,675 and 5,607,669.

The salt of an alkylated and cross linked polymer comprising the reaction product of: (a) one or more cross linked polymers, or salts and copolymers thereof having a repeat unit selected from the group consisting of: $(NR-CH_2CH_2)n$ (2) and $(NR-CH_2CH_2-NR-CH_2CH_2-NR-CH_2CHOH-CH_2)n$ (3) where n is a positive integer and each R, independently, is H or a C1-C8 alkyl group; (b) at least one aliphatic alkylating agent, said reaction product characterized in that: (i) at least some of the nitrogen atoms in said repeat units unreacted with said alkylating agent; (ii) less than 10 mol percent of the nitrogen atoms in said repeat units reacting with said alkylating agent forming quaternary ammonium units; and (iii) a fixed positive charge and one or more counter ions, such as Colesevelam and colesevelam hydrochloride.

Useful bile acid binders in accordance with the invention are resins, such as cholestyramine and cholestipol. One advantage is that the dose of bile acid binder might be kept lower than the therapeutic dose for treatment of cholesterolaemia in single treatment comprising solely a bile acid binder. By a low dose of bile acid binder any possible side effects caused by poor tolerance of the patient to the therapeutic dose could also be avoided.

Another useful bile acid binder is a water insoluble non-toxic polymeric amine having a molecular weight in excess of 3,000, having the property of binding at least 30% of the available glycocholic acid within 5 minutes when exposed to an aqueous solution of an equal weight of said acid, having a polymer skeleton inert to digestive enzymes, and having a water content greater than 65% after equilibration with air at 100% relative humidity, e.g., cholestipol described in U.S. Pat. No. 3,383,281, In a further aspect of the invention a suitable bile acid binder is one of cholestyramine, cholestipol or colesevelam.

A preferred aspect of the present invention is the use of colesevelam as the bile acid binder.

The compositions of the invention may further comprise statins e.g. an HMG Co-A reductase inhibitor, or a pharmaceutically acceptable salt, solvate, solvate of such a salt or a prodrug thereof, in association with a pharmaceutically acceptable diluent or carrier.

One embodiment of the invention relates to a combined oral pharmaceutical formulation comprising an IBAT inhibitor compound of formula (I) or Formula (II) as defined above or a pharmaceutically acceptable salt, solvate, solvate of such a salt or a prodrug thereof and a bile acid binder or a pharmaceutically acceptable salt, solvate, solvate of such a salt or a prodrug thereof, said formulation being designed to deliver the bile acid binder in the colon and the IBAT inhibitor in the small intestine.

One embodiment of the present invention is a pharmaceutical formulation comprising a core of a bile acid binder formulated for release in the colon, surrounded by an outer layer comprising an IBAT inhibitor of formula (I) or Formula (II) as defined above, and formulated for immediate release or for delayed release in the distal jejunum or the proximal ileum.

Statins

In another aspect of the invention, an IBAT inhibitor compound e.g. a compound of formula (I) or formula (II) as defined above or a pharmaceutically acceptable salt, solvate, solvate of such a salt or a prodrug thereof, may be administered in association with an HMG Co-A reductase inhibitor, or pharmaceutically acceptable salts, solvates, solvates of such salts or prodrugs thereof. Suitable HMG Co-A reductase inhibitors, pharmaceutically acceptable salts, solvates, solvates of such salts or prodrugs thereof are statins well known in the art. Particular statins are fluvastatin, lovastatin, pravastatin, simvastatin, atorvastatin, cerivastatin, bervastatin, dalvastatin, mevastatin and (E)-7-[4-(4-fluorophenyl)-6-isopropyl-2-[methyl (methylsulphonyl) amino] pyrimidin-5-yl] (3R,5S)-3,5-dihydroxyhept-6-enoic acid (rosuvastatin), or a pharmaceutically acceptable salt, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A further particular statin is (E)-7-[4-(4-fluorophenyl)-6-isopropyl-2-[methyl (methylsulphonyl) amino] pyrimidin-5-yl] (3R,5S)-3,5-dihydroxyhept-6-enoic acid (rosuvastatin), or a pharmaceutically acceptable salt, solvate, solvate of such a salt or a prodrug thereof. Other particular statin are rosuvastatin calcium salt and pitavastatin (HMG Co A reductase).

In an additional aspect of the invention, the compound of formula (I) or formula (II) as defined above, or a pharmaceutically acceptable salt, solvate, solvate of such a salt or a prodrug thereof may be administered in association with an HMG Co-A reductase inhibitor, or a pharmaceutically acceptable salt, solvate, solvate of such a salt or a prodrug thereof, and/or a bile acid binder thereby avoiding a possible risk of excess of bile acids in colon caused by the inhibition of the ileal bile acid transport system. An excess of bile acids in the visceral contents may cause diarrhoea. Thus, the present invention also provides a treatment of a possible side effect such as diarrhoea in patients during therapy comprising a compound of formula (I) or formula (II) as defined above, or a pharmaceutically acceptable salt, solvate, solvate of such a salt or a prodrug thereof.

An HMG CoA-reductase inhibitor, or a pharmaceutically acceptable salt, solvate, solvate of such a salt or a prodrug thereof will by its action decrease the endogenous cholesterol available for the bile acid synthesis and have an additive effect in combination with a compound of formula (I) or formula (II) as defined above, or a pharmaceutically acceptable salt, solvate, solvate of such a salt or a prodrug thereof on lipid lowering.

The composition may further comprise a PPAR alpha and/or gamma agonist, or a pharmaceutically acceptable salt thereof.

A CETP (cholesteryl ester transfer protein) inhibitor, for example those referenced and described in WO 00/38725 page 7 line 22-page 10, line 17 which are incorporated herein by reference.

A cholesterol absorption antagonist for example azetidinones such as SCH 58235 and those described in U.S. Pat. No. 5,767,115 which are incorporated herein by reference; MTP (microsomal transfer protein) inhibitor for example those described in Science, 282, 751-54, 1998 which are incorporated herein by reference;

A fibric acid derivative; for example clofibrate, gemfibrozil, fenofibrate, ciprofibrate and bezafibrate;

A nicotinic acid derivative, for example, nicotinic acid (niacin), acipimox and niceritrol;

A phytosterol compound for example stanols;

Probucol;

An anti-obesity compound for example orlistat (EP 129,748) and sibutramine (GB 2,184,122 and U.S. Pat. No. 4,929,629);

An antihypertensive compound for example an angiotensin converting enzyme (ACE) inhibitor, an angiotensin II receptor antagonist, an adrenergic blocker, an alpha adrenergic blocker, a beta adrenergic blocker, a mixed alpha/beta adrenergic blocker, an adrenergic stimulant, calcium channel blocker, a diuretic or a vasodilator;

Insulin;

Sulphonylureas including glibenclamide and/or tolbutamide.

Biguanides

In some embodiments, the additional therapeutic agent is a biguanide. In some instances, biguanides reduce blood and/or plasma glucose levels. Examples of biguanides include and are not limited to metformin, buformin, phenformin, proguanil or the like.

Acarbose;

or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Angiotensin II Antagonists

Preferred angiotensin II antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, tasosartan, telmisartan and eprosartan. Particularly preferred angiotensin II antagonists or pharmaceutically acceptable derivatives thereof for use in the present invention are candesartan and candesartan cilexetil.

PPAR alpha and/or gamma and/or delta agonists or a pharmaceutical acceptable salt thereof.

In another aspect of the invention, the IBAT inhibitor compound, or a pharmaceutically acceptable salt, solvate, solvate of such a salt or a prodrug thereof, may be administered in association with a PPAR alpha and/or gamma agonist, or pharmaceutically acceptable salts, solvates, solvates of such salts or prodrugs thereof. Suitable PPAR alpha and/or gamma agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma agonist refers to WY-14643, clofibrate, fenofibrate, bezafibrate, GW 9578, troglitazone, pioglitazone, rosiglitazone, eglitazone, proglitazone, BRL-49634, KRP-297, JTT-501, SB 213068, GW 1929, GW 7845, GW 0207, L-796449, L-165041 and GW 2433.

Particularly a PPAR alpha and/or gamma agonist refers to (S)-2-ethoxy-3-[4-(2-{4-methanesulphonyloxyphenyl} ethoxy) phenyl] propanoic acid and pharmaceutically acceptable salts thereof.

According to one embodiment the substances of the invention are used together with one or more antidiabetics hypoglycaemic active ingredients, cholesterol absorption inhibitors, PPAR delta agonists, fibrates, MTP inhibitors, bile acid absorption inhibitors, polymeric bile acid adsorbents, LDL receptor inducers, ACAT inhibitors, antioxidants, lipoprotein lipase inhibitors, ATP-citrate lyase inhibitors, squalene synthetase inhibitors, lipoprotein(a) antagonists, HM74A receptor agonists, lipase inhibitors, insulins, sulfonylureas, biguanides, meglitinides, thiazolidinediones, alpha-glucosidase inhibitors, active ingredients which act on the ATP-dependent potassium channel of the beta cells, glycogen phosphorylase inhibitors, glucagon receptor antagonists, activators of glucokinase, inhibitors of gluconeogenesis, inhibitors of fructose-1,6-bisphosphatase, modulators of glucose transporter 4, inhibitors of glutamine-fructose-6-phosphate amidotransferase, inhibitors of dipeptidylpeptidase IV, inhibitors of 11-beta-hydroxysteroid dehydrogenase 1, inhibitors of protein tyrosine phosphatase 1B, modulators of the sodium-dependent glucose transporter 1 or 2, modulators of GPR40, inhibitors of hormone-sensitive lipase, inhibitors of acetyl-CoA carboxylase, inhibitors of phosphoenolpyruvate carboxykinase, inhibitors of glycogen synthase kinase-3 beta, inhibitors of protein kinase C beta, endothelin-A receptor antagonists, inhibitors of I kappaB kinase, modulators of the glucocorticoid receptor, CART agonists, NPY agonists, MC4 agonists, orexin agonists, H3 agonists, TNF agonists, CRF agonists, CRF BP antagonists, urocortin agonists, beta 3 agonists, CB1 receptor antagonists, MSH (melanocyte-stimulating hormone) agonists, CCK agonists, serotonin reuptake inhibitors, mixed serotoninergic and noradrenergic compounds, 5HT agonists, bombesin agonists, galanin antagonists, growth hormones, growth hormone-releasing compounds, TRH agonists, uncoupling protein 2 or 3 modulators, leptin agonists, DA agonists (bromocriptine, Doprexin), lipase/amylase inhibitors, PPAR modulators, RXR modulators or TR-beta agonists or amphetamines.

One aspect of the invention is a method for the treatment of a liver disease, whereby an IBAT inhibitor of Formula (I) or Formula (II) as defined above is brought into contact with the distal ileum of an individual in need of such treatment.

In one embodiment of the invention, an IBAT inhibitor of Formula (I) or Formula (II) as defined above, is administered in combination with a second therapeutic agent selected from a DPP-IV inhibitor, a thiazolidinedione, or an analogue thereof, or a TGR5 agonist.

In certain embodiments, IBAT inhibitor compounds described herein are combined with or utilized in combination with one or more of the following therapeutic agents in any combination: insulin, insulin-mimetics, DPP-IV inhibitors, or TGR5 modulators.

Further active substances to be combined with one or more IBAT inhibitors of the invention may be chosen from one or more of the following substances:
Ursodeoxycholic acid; nor-ursodeoxycholic acid; Rifampicin and related rifamycin derivatives as described in U.S. Pat. No. 3,342,810; opiat antagonists such as Naloxone and Naltrexone; serotonin antagonists such as 5-HT3 receptor antagonists and 5 HT2 antagonists, e.g. Trazodone, Nefazodone, Amoxapine, Clozapine; antihistamines such as Brompheniramine, Chlorpheniramine Dimenhydrinate, Diphenhydramine, Doxylamine Loratadine Cetirizine; serotonin reuptake inhibitors such as Citalopram, Dapoxetine, Escitalopram, Fluoxetine, Fluvoxamine, Indalpine, Paroxetine, Sertraline, Zimelidine; corticosteroids such as glucocorticoids and mineralocorticoids e.g. chosen from Hydrocortisone (Cortisol), Cortisone and acetate, Prednisone, Prednisolone, Methylprednisolone, Dexamethasone, Betamethasone, Triamcinolone, Beclometasone, Fludrocortisone and acetate, Deoxycorticosterone and acetate (DOCA) Aldosterone.

Examples of PPAR delta agonists are GW-501516 (501516, GSK-516, GW-516, GW-1516; a peroxisome proliferator-activated receptor (PPAR)-delta agonist, and several other compounds developed from GW-501516, including GI-262570, GW-0072, GW-7845 and GW-7647.

According to one embodiment the BAT inhibitor may be combined with one or more of Atreleuton, Eprotirome, Losmapimod, Ezetimibe (SCH58235) Bezafibrate, Fenofibrate, Varespladib, Darapladib, Lomitapide, Implitapide, Rosiglitazone, Dalcetrapib, Anacetrapib, Lorcaserin, Dapagliflozin, Canagliflozin, Sergliflozin ASP-1941 Orlistat, Pioglitazone, Sodelglitazar, Netoglitazone, Indeglitazar, Naveglitazar, Lobeglitazone, Aleglitazar, Bromocriptine, Tesofensine, Monoamine, Alogliptin, Vildagliptin, Saxagliptin, Sitagliptin, Denagliptin, Gemigliptin, Linagliptin, Dutogliptin, Teneligliptin, LC-150444, Laropiprant extended release niacin, Simvastatin ezetimibe, Rosuvastatin fenofibrate, Rosuvastatin ezetimibe and Atorvastatin ezetimibe.

Combinations with Tredaptive, Vytorin and Certriad may be used.

According to one embodiment the IBAT inhibitor may be combined with one or more of any of the above mentioned other compounds.

According to one embodiment the IBAT inhibitors of the present invention are combined with at least one other active substance selected from dipeptidyl peptidase-IV-inhibitors, PPAR γ agonists, statins and bile acid binders in any combination.

According to one embodiment the IBAT inhibitors of the present invention are combined with at least one DPPIV, at least one PPAR γ agonist, such as Sitagliptin and Pioglitazon.

According to one other embodiment the IBAT inhibitors of the present invention are combined with at least one DPPIV and at least one statin e.g. Sitagliptin and Simvastatin.

Another active substance which may be combined with the IBAT inhibitors of the invention is ursodeoxycholic acid.

According to one embodiment the invention relates to a composition comprising one or more IBAT inhibitors of the invention and cholestyramin and/or colesevelam and/or cholistipol.

According to one embodiment the invention relates to a composition comprising one or more of the compounds of Example 1, 2, 3, 4, 5, 6, 7, 8, 9, 10, 11, 12, 13 and 14 and cholestyramin and/or colesevelam and/or cholistipol.

According another embodiment the invention relates to a composition comprising one or more of the compounds of 1,1-Dioxo-3,3-dibutyl-5-phenyl-7-methylthio-8-(N—{(R)-1'-phenyl-1'-[N'-(carboxymethyl)-carbamoyl] methyl}carbamoylmethoxy)-2,3,4,5-tetrahydro-1,5-benzothiazepine (Example 5) and cholestyramin and/or colesevelam and/or cholistipol.

According another embodiment the invention relates to a composition comprising one or more of the compounds of 1,1-Dioxo-3,3-dibutyl-5-phenyl-7-methylthio-8-(N—{(R)-α-[N—((S)-1-carboxy-2-methylpropyl)carbamoyl]-4-hydroxybenzyl}carbamoylmethoxy)-2,3,4,5-tetrahydro-1,2,5-benzothiadiazepine (Example 13), and cholestyramin and/or colesevelam and/or cholestipol.

According another embodiment the invention relates to a composition comprising one or more of the compounds of 1,1-Dioxo-3,3-dibutyl-5-phenyl-7-methylthio-8-(N—{(R)-1'-phenyl-1'-[N'-(carboxymethyl) carbamoyl] methyl} carbamoylmethoxy)-2,3,4,5-tetrahydro-1,5-benzothiazepine (Example 14) and cholestyramin and/or colesevelam and/or cholestipol.

Carriers and Excipients

The compositions of the invention may further comprise a pharmaceutically acceptable diluent or carrier.

Pharmaceutical compositions may be formulated as known in the art using one or more physiologically acceptable carriers including, e.g., excipients and depending on the route of administration chosen.

A carrier includes, in some embodiments, a pharmaceutically acceptable excipient and is selected on the basis of compatibility with compounds described herein, such as, compounds of any of Formula I and II, and the release profile properties of the desired dosage form.

Exemplary carrier materials include, e.g., binders, suspending agents, disintegration agents, filling agents, surfactants, solubilizers, stabilizers, lubricants, wetting agents, diluents.

Pharmaceutical compositions and carriers are described, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

A mixture of a compound of Formula I and II and possibly also other active compounds mentioned herein, with other chemical components, such as carriers, stabilizers, diluents, dispersing agents, suspending agents, thickening agents, and/or excipients may be formulated into a composition. In certain embodiments, therapeutically effective amounts of compounds described herein are administered in a pharmaceutical composition to an individual having a disease, disorder, or condition to be treated. In specific embodiments, the individual is a human. The compounds described herein are either utilized separately or in combination with one or more additional therapeutic agents.

In certain embodiments, the pharmaceutical formulations described herein are administered to an individual in any manner, including one or more of multiple administration routes, such as, by way of non-limiting example, oral, parenteral (e.g., intravenous, subcutaneous, intramuscular), intranasal, buccal, topical, rectal, or transdermal administration routes.

The pharmaceutical compositions described herein are formulated as a dosage form. As such, in some embodiments, provided herein does a dosage form comprise a compound described herein, suitable for administration to an individual. In certain embodiments, suitable dosage forms include, by way of non-limiting example, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

The pharmaceutical solid dosage forms described herein optionally include an additional therapeutic compound described herein and one or more pharmaceutically acceptable additives such as a compatible carrier, binder, filling agent, suspending agent, flavouring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in Remington's Pharmaceutical Sciences, 20th Edition (2000), a film coating is provided around the formulation of the compound of Formula I-II. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

Method of Treatment

The invention also regards a method for treatment and/or prophylaxis of a liver disease, in a warm-blooded animal, such as man, in need of such treatment and/or prophylaxis comprising administering an effective amount of a compound or a composition according to the invention to the individual.

A method for treating any of the diseases or conditions described herein in an individual in need of such treatment, may involve administration of pharmaceutical compositions containing at least one IBAT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

Dosage Forms

The pharmaceutical solid dosage forms may optionally include additional therapeutic compounds and one or more pharmaceutically acceptable additives such as a compatible carrier, binder, filling agent, suspending agent, flavouring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some aspects, using standard coating procedures, such as those described in Remington's Pharmaceutical Sciences, 20th Edition (2000), a film coating is provided around the formulation of the compound of Formula I-II. In one embodiment, a compound described herein is in the form of a particle and some or all of the particles of the compound are coated. In certain embodiments, some or all of the particles of a compound described herein are microencapsulated. In some embodiments, the particles of the compound described herein are not microencapsulated and are uncoated.

An IBAT inhibitor of Formula I and II may be used in the preparation of medicaments for the prophylactic and/or therapeutic treatment of obesity and/or diabetes. A method for treating any of the diseases or conditions described herein in an individual in need of such treatment, involves administration of pharmaceutical compositions containing at least one IBAT inhibitor described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said individual.

A dosage form comprises a matrix that allows for controlled release of an active agent in the distal jejunum, proximal ileum, distal ileum and/or the colon. In some embodiments, a dosage form comprises a polymer that is pH sensitive (e.g., a MMX™ matrix from Cosmo Pharmaceuticals) and allows for controlled release of an active agent in the ileum and/or the colon. Examples of such pH sensitive polymers suitable for controlled release include and are not limited to polyacrylic polymers (e.g., anionic polymers of methacrylic acid and/or methacrylic acid esters, e.g., Carbopol® polymers, (CAS number 9063-87-0) that comprise acidic groups (e.g., —COOH, —SO$_3$H) and swell in basic pH of the intestine (e.g., pH of about 7 to about 8). In some embodiments, a dosage form suitable for controlled release in the distal ileum comprises microparticulate active agent (e.g., micronized active agent). In some embodiments, a non-enzymatically degrading poly(dl-lactide-co-glycolide) (PLGA) core is suitable for delivery of an IBAT to the distal ileum. In some embodiments, a dosage form comprising an IBAT is coated with an enteric polymer (e.g., Eudragit® S-100, cas number 25086-15-1), cellulose acetate phthalate, polyvinylacetate phthalate, hydroxypropylmethylcellulose phthalate, anionic polymers of methacrylic acid, methacrylic acid esters or the like) for site specific delivery to the ileum and/or the colon. In some embodiments, bacterially activated systems are suitable for targeted delivery to the ileum. Examples of micro-flora activated systems include dosage forms comprising pectin, galactomannan, and/or Azo hydrogels and/or glycoside conjugates (e.g., conjugates of D-galactoside, beta-D-xylopyranoside or the like) of the active agent. Examples of gastrointestinal micro-flora enzymes include bacterial glycosidases such as, for example, D-galactosidase, beta-D-glucosidase, alpha-L-arabinofuranosidase, beta-D-xylopyranosidase or the like.

Coated units may be filled into hard gelatine capsules or mixed with tablet excipients, such as fillers, binders, disintegrants, lubricants and other pharmaceutically acceptable additives, and be compressed into tablets. The compressed tablet is optionally covered with film-forming agents to obtain a smooth surface of the tablet and further enhance the mechanical stability of the tablet during packaging and transport. Such a tablet coat, which may be applied on a multiple unit tablet or a conventional tablet, may further comprise additives like anti-tacking agents, colorants and pigments or other additives to improve the tablet appearance.

Suitable drugs for the new formulations are IBAT inhibitor compounds such as described in the above-discussed documents, hereby incorporated by references.

The IBAT inhibitor compound could alternatively be a low permeability drug as defined in the Biopharmaceutical Classification System proposed by FDA.

A combination therapy according to the invention should preferably comprise simultaneously, separately or sequentially administration of an IBAT inhibitor compound and a bile acid binder. The IBAT inhibitor could preferably be formulated for ileum delivery and the bile acid binder could preferably be formulation for colon release.

Dosage

The compound of formula (I), or a pharmaceutically acceptable salt, solvate, solvate of such a salt or a prodrug thereof, will normally be administered to a warm-blooded animal at a unit dose within the range 5-5000 mg per square meter body area of the animal, i.e. approximately 0.1-100 mg or 0.01-50 mg, and this normally provides a therapeutically-effective dose. A unit dose form such as a tablet or capsule will usually contain, for example 1-250 mg of active ingredient. Preferably a daily dose in the range of 1-50 mg is employed. In another aspect a daily dose in the rage of 0.02-20 mg is employed. However the daily dose will necessarily be varied depending upon the host treated, the particular route of administration, and the severity of the illness being treated.

Accordingly the optimum dosage may be determined by the practitioner who is treating any particular patient.

The size of the dose required for the therapeutic or prophylactic treatment will necessarily be varied depending on the host treated, the route of administration and the severity of the illness being treated. A unit dose in the range, for example, 1-100, preferably 1-50 is envisaged. The daily dose can be administered as a single dose or divided into one, two, three or more unit doses.

A pharmaceutical formulation according to the present invention with a targeted delivery in the gastro intestinal tract provides a reduced systemic exposure, as can be measured by the area under the drug plasma concentration versus time curve (AUC) or 7α-hydroxy-4-cholesten-3-one (C4), while maintaining or even increasing the therapeutic effect, as e.g. measured by serum cholesterol reduction.

A combination therapy comprising an IBAT inhibitor and a bile acid binder comprises preferably a low daily dose of the bile acid binder, such as less than 5 g of a resin, and more preferably less than 2 g. A dosage form with colon release of the bile acid binder could be constructed by any of the above described principles for delayed release formulations.

A combination therapy comprising an IBAT inhibitor and a bile acid binder may comprise a low daily dose of the bile acid binder, such as less than 5 g of a resin, and more preferably less than 4, 3, 2 or less than 1 g. Suitable ranges may be 0.1-5 g, 0.5-4 g, 1-3 g, 2-4 g, 2-3 g per day. A dosage form with colon release of the bile acid binder could be constructed by any of the above described principles for delayed release formulations.

A tablet may consist of an inner core of 1-1000 mg, e.g. 200-800 mg, 10-400 mg, 10-200 mg or 20-80 mg acid binder in a colonic delivery formulation and an outer lamina with 1-100 mg, 5-50 mg e.g. 1-20 mg of an IBAT inhibitor.

The daily dose of IBAT inhibitor and/or bile acid binder can be administered as a single dose or divided into one, two, three or more unit doses.

Dosing three times a day with 400 mg of colesevelam in a colonic release formulation will give an adequate binding of bile acids in the colon as the total luminal volume is expected to be about 100 ml, which is in accordance to an accepted pharmacokinetic calculation volume of 250 to 300 ml for the small gut. The daily recommended total dose of colesevelam to block bile acid absorption in total gut of humans is 3750 mg/day.

Kit

Further, the invention relates to a kit comprising compound or a composition according to the invention and possibly also an instruction for use.

According to a further aspect of the present invention there is provided a kit comprising an IBAT inhibitor according to the invention or a pharmaceutically acceptable salt, solvate, solvate of such a salt or a prodrug thereof, and an instruction for use.

According to a further aspect of the present invention there is provided a kit comprising an IBAT inhibitor according to the invention or a pharmaceutically acceptable salt, solvate, solvate of such a salt or a prodrug thereof, and any of the above mentioned substances for use in combination, or a pharmaceutically acceptable salt, solvate, solvate of such a salt or a prodrug thereof.

According to a further aspect of the present invention there is provided a kit comprising: a) an IBAT inhibitor according to the invention or a pharmaceutically acceptable salt, solvate, solvate of such a salt or a prodrug thereof, in a first unit dosage form; b) any of the above mentioned substances for use in combination or a pharmaceutically acceptable salt, solvate, solvate of such a salt or a prodrug thereof; in a second unit dosage form; and c) container means for containing said first and second dosage forms.

The following contemplated Examples are intended to illustrate, but in no way limit the scope of the invention. All references cited herein are hereby incorporated by reference in their entirety.

The expression "comprising" as used herein should be understood to include, but not be limited to, the stated items.

Example 1

1,1-Dioxo-3,3-dibutyl-5-phenyl-7-methylthio-8-(N—{(R)-α-[N-(carboxymethyl)carbamoyl]benzyl}carbamoylmethoxy)-2,3,4,5-tetrahydro-1,2,5-benzothiadiazepine, Mw. 696.89. This compound is prepared as described in Example 2 of WO3022286.

Example 2

1,1-Dioxo-3,3-dibutyl-5-phenyl-7-methylthio-8-(N—{(R)-α-[N'—((S)-1-carboxyethyl)carbamoyl]benzyl}carbamoylmethoxy)-2,3,4,5-tetrahydro-1,5-benzothiazepine, Mw. 709.92.

This compound is prepared as described in Example 2 of WO03106482.

Example 3

1,1-Dioxo-3,3-dibutyl-5-phenyl-7-methylthio-8-(N—{(R)-α-[N—((S)-1-carboxypropyl)carbamoyl]benzyl}carbamoylmethoxy)-2,3,4,5-tetrahydro-1,2,5-benzothiadiazepine, Mw. 724.94.

This compound is prepared as described in Example 6 of WO3022286.

Example 4

1,1-Dioxo-3,3-dibutyl-5-phenyl-7-methylthio-8-(N—{(R)-α-[N—((R)-1-carboxy-2-methylthioethyl)carbamoyl]benzyl}carbamoylmethoxy)-2,3,4,5-tetrahydro-1,2,5-benzothiadiazepine, Mw. 757.01.

This compound is prepared as described in Example 7 of WO3022286.

Example 5

1,1-Dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine, Mw. 740.94.

This compound is prepared as described in Example 29 of WO3022286.

Example 6

1,1-Dioxo-3,3-dibutyl-5-phenyl-7-methylthio-8-(N—{(R)-α-[N—((R)-1-carboxy-2-methylthio-ethyl)carbamoyl]-4-hydroxybenzyl}carbamoylmethoxy)-2,3,4,5-tetrahydro-1,2,5-benzothiadiazepine, Mw. 773.00.

This compound is prepared as described in Example 30 of WO3022286.

Example 7

1,1-Dioxo-3,3-dibutyl-5-phenyl-7-methylthio-8-(N—{(R)-α-[N—((S)-1-carboxy-2-methylpropyl)carbamoyl]benzyl}carbamoylmethoxy)-2,3,4,5-tetrahydro-1,2,5-benzothiadiazepine, Mw. 738.97.

This compound is prepared as described in Example 15 of WO3022286.

Example 8

1,1-Dioxo-3,3-dibutyl-5-phenyl-7-methylthio-8-(N—{(R)-α-[N—((S)-1-carboxy-2-(R)-hydroxypropyl)carbamoyl]-4-hydroxybenzyl}carbamoylmethoxy)-2,3,4,5-tetrahydro-1,2,5-benzothiadiazepine, Mw. 756.94.

This compound is prepared as described in Example 26 of WO3022286.

Example 9

1,1-Dioxo-3,3-dibutyl-5-phenyl-7-methylthio-8-(N—{(R)-α-[N—((S)-1-carboxybutyl)carbamoyl]-4-hydroxybenzyl}carbamoylmethoxy)-2,3,4,5-tetrahydro-1,2,5-benzothiadiazepine, Mw. 754.97.

This compound is prepared as described in Example 28 of WO3022286.

Example 10

1,1-Dioxo-3,3-dibutyl-5-phenyl-7-methylthio-8-(N—{(R)-α-[N—((S)-1-carboxyethyl)carbamoyl]benzyl}carbamoylmethoxy)-2,3,4,5-tetrahydro-1,2,5-benzothiadiazepine, Mw. 710.91.

This compound is prepared as described in Example 5 of WO3022286.

Example 11

1,1-Dioxo-3,3-dibutyl-5-phenyl-7-methylthio-8-(N—{(R)-α-[N'—((S)-1-carboxypropyl)carbamoyl]-4-hydroxybenzyl}carbamoylmethoxy)-2,3,4,5-tetrahydro-1,5-benzothiazepine, Mw. 739.95.

This compound is prepared as described in Example 1 of WO3022286.

Example 12

1,1-Dioxo-3,3-dibutyl-5-phenyl-7-methylthio-8-(N—{(R)-α-[N—((S)-1-carboxyethyl)carbamoyl]-4-hydroxybenzyl}carbamoylmethoxy)-2,3,4,5-tetrahydro-1,2,5-benzothiadiazepine, Mw. 726.91.

This compound is prepared as described in Example 11 of WO3022286.

Example 13

1,1-Dioxo-3,3-dibutyl-5-phenyl-7-methylthio-8-(N—{(R)-α-[N—((S)-1-carboxy-2-methylpropyl)carbamoyl]-4- hydroxybenzyl}carbamoylmethoxy)-2,3,4,5-tetrahydro-1,2,5-benzothiadiazepine, Mw. 754.97.

This compound is prepared as described in Example 27 of WO3022286.

Example 14

1,1-Dioxo-3,3-dibutyl-5-phenyl-7-methylthio-8-(N—{(R)-1'-phenyl-1'-[N'-(carboxymethyl)carbamoyl]methyl}carbamoylmethoxy)-2,3,4,5-tetrahydro-1,5-benzothiazepine, Mw. 695.90.

This compound is prepared as described in Example 43 of WO0250051.

Example 15

Pharmaceutical Effect Mean Inhibitory Effect (%)

ISBT Hu HEK Uptake SPA 13203 IBAT HUM Ileal Bile Acid Transporter Human HEK Glycocholic acid Uptake Radiometric—SPA Inhibitor IC50 Mean IC50 (nM) was determined for the compounds of examples 1-14

Test System

Animals

Species Mouse; Strain ApoE knock out; Sub strain C57BL/6; Sex Female; Total No. of animals 70; Body weight range 20 g to 22 g; Supplier Möllegaard's Breeding (Skensved, Denmark); Identification method ID cards (bar code).

Acclimatisation At least one week at the Section of Laboratory; Animal Resource at AstraZeneca; Housing conditions Kept five by five in cages (Makrolon III, 7 dm2) in a room with regulated temperature (22° C.), relative humidity (40% to 60%) and a 12/12 hours light/dark cycle. Diet Free access to R3 pellets (Lactamin, Vadstena, Sweden) during the housing and experimental period. Water, free access to tap water during the housing and experimental period.

Bedding Sprinkle bedding of aspen wood (Tapvei, Finland).

Experimental Procedures

The animals were orally administered vehicle (n=3) or the compound of Example 14 (0.156 (n=3), 0.625 (n=3) or 2.5 μmol/kg (n=3)) at 13:00 o'clock on the experimental day. Thirty minutes later, a trace amount of $^{75}$SeHCAT ($^{75}$Se-homo-tauro-cholic acid) (0.1 mCi per 0.1 mL per mouse) was orally given to each mouse. Twenty-four hours after $^{75}$SeHCAT administration, the animals were killed by CO2 inhalation. At sacrifice, the gall bladder and the whole intestine were removed, and the faeces during the 24-hour period after $^{75}$SeHCAT administration was collected for each mouse. The gamma radioactivities of $^{75}$SeHCAT in the faeces and in the gall bladder-intestine were separately counted by 1282 CompuGamma CS Gamma counter (Wallac oy, Turku, Finland). The stability as well as the quantity of the $^{75}$SeHCAT administered to each mouse, were controlled with an additional $^{75}$SeHCAT aliquot following the same experimental process as other tested samples in the study.

Data Analysis

The sum of the gamma counts from both the faeces and the gall bladder-intestine was considered as the total recovered $^{75}$SeHCAT, which was averaged around 85% of the total $^{75}$SeHCAT administered to each mouse. Of the recovered radioactivity of $^{75}$SeHCAT, the percentage of the $^{75}$SeHCAT detected in the faeces was considered as the faecal excretion while that in the gall bladder-intestine as body retention. Inhibitory effect of the compound of Example 14 on $^{75}$SeHCAT intestinal absorption was calculated following the $^{75}$SeHCAT body retention and the faecal excretion, and the ED50 of the compound was estimated following the dose-effect curve.

Results

The mean IBAT inhibitory effect (%) at a dose (μmol/kg): 0.156 was determined for the compounds of examples 1-14 and is reported in Table 1.

TABLE 1

| Example | Structure | % inhibition 0.156 μmol/kg | Mean IC50 nM |
|---|---|---|---|
| 1. | 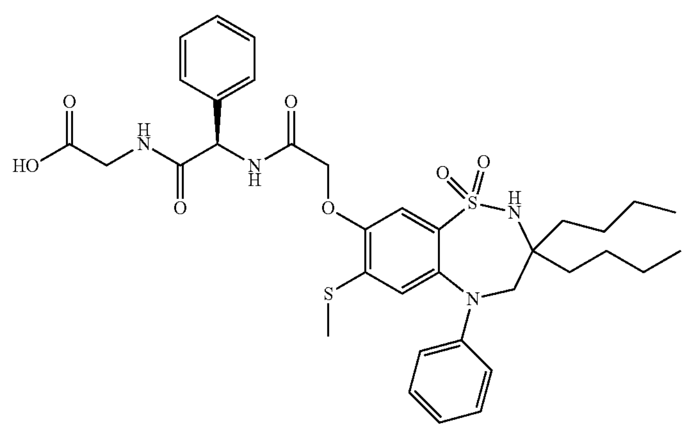 [SMILES: CCCCC1(CCCC)CN(c2ccccc2)c2cc(SC)c(OCC(=O)N[C@@H](C(=O)NCC(=O)O)c3ccccc3)cc2S(=O)(=O)N1] | 43 | 0.45 |

TABLE 1-continued

| Example | Structure | % inhibition 0.156 µmol/kg | Mean IC50 nM |
|---|---|---|---|
| 2. | 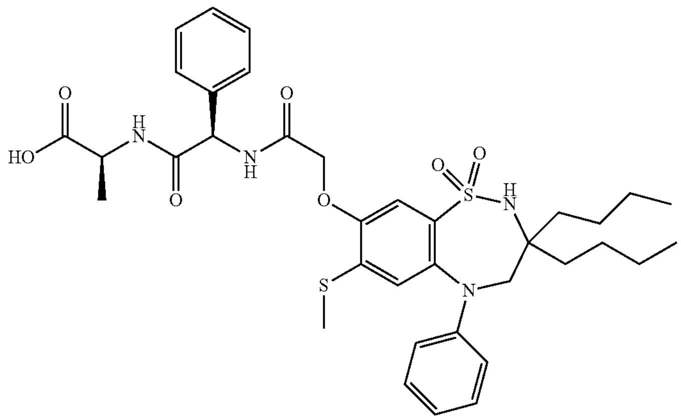 [SMILES: CCCCC1(CCCC)CN(c2ccccc2)c2cc(SC)c(OCC(=O)N[C@@H](C(=O)N[C@@H](C)C(=O)O)c3ccccc3)cc2S(=O)(=O)N1] | 55 | 0.39 |
| 3. | 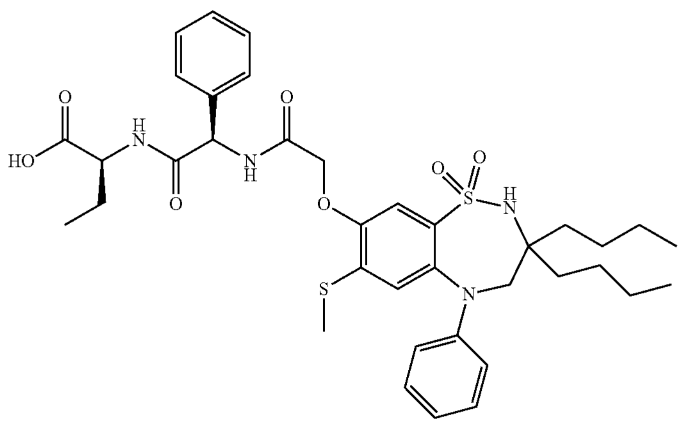 [SMILES: CCCCC1(CCCC)CN(c2ccccc2)c2cc(SC)c(OCC(=O)N[C@@H](C(=O)N[C@@H](CC)C(=O)O)c3ccccc3)cc2S(=O)(=O)N1] | 63 | 0.18 |
| 4. | 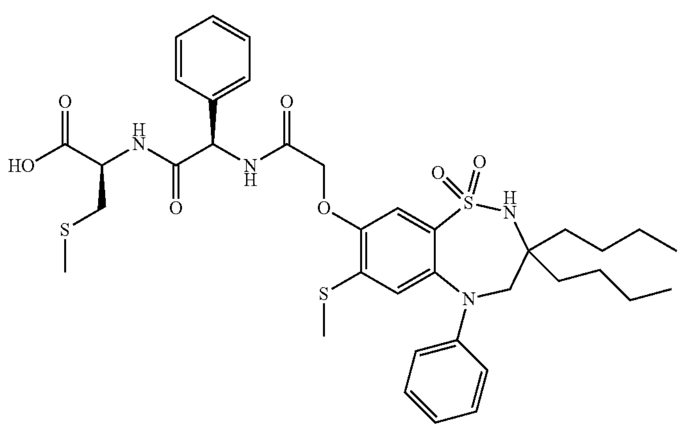 [SMILES: CCCCC1(CCCC)CN(c2ccccc2)c2cc(SC)c(OCC(=O)N[C@@H](C(=O)N[C@@H](CSC)C(=O)O)c3ccccc3)cc2S(=O)(=O)N1] | 63 | 0.35 |

TABLE 1-continued
| Example | Structure | % inhibition 0.156 µmol/kg | Mean IC50 nM |
|---|---|---|---|
| 5. | 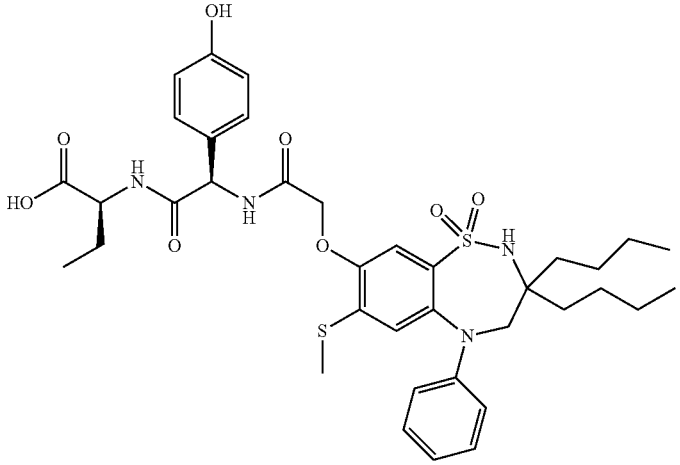 [SMILES: CCCCC1(CCCC)CN(c2ccccc2)c2cc(SC)c(OCC(=O)N[C@@H](C(=O)N[C@@H](CC)C(=O)O)c3ccc(O)cc3)cc2S(=O)(=O)N1] | 74 | 0.16 |
| 6. | 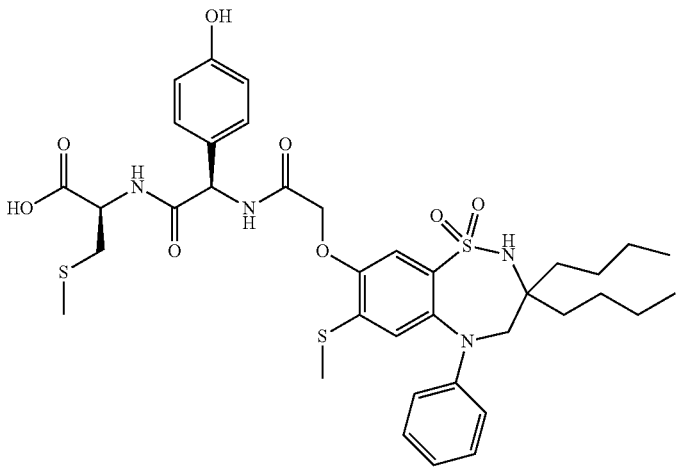 [SMILES: CCCCC1(CCCC)CN(c2ccccc2)c2cc(SC)c(OCC(=O)N[C@@H](C(=O)N[C@@H](CSC)C(=O)O)c3ccc(O)cc3)cc2S(=O)(=O)N1] | 59 | — |
| 7. | 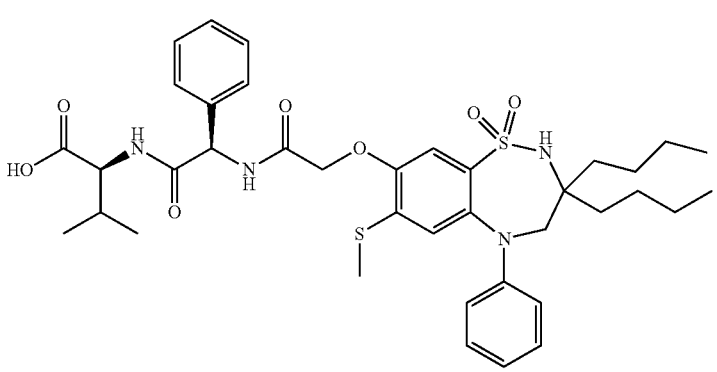 [SMILES: CCCCC1(CCCC)CN(c2ccccc2)c2cc(SC)c(OCC(=O)N[C@@H](C(=O)N[C@H](C(=O)O)C(C)C)c3ccccc3)cc2S(=O)(=O)N1] | 66 | 0.36 |

TABLE 1-continued
| Example | Structure | % inhibition 0.156 µmol/kg | Mean IC50 nM |
|---|---|---|---|
| 8. | 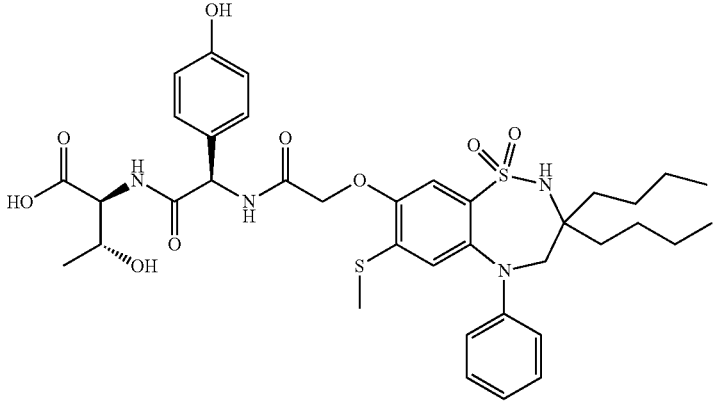 [SMILES: CCCCC1(CCCC)CN(c2ccccc2)c2cc(SC)c(OCC(=O)N[C@@H](C(=O)N[C@H](C(=O)O)[C@@H](C)O)c3ccc(O)cc3)cc2S(=O)(=O)N1] | 46 | 0.11 |
| 9. | 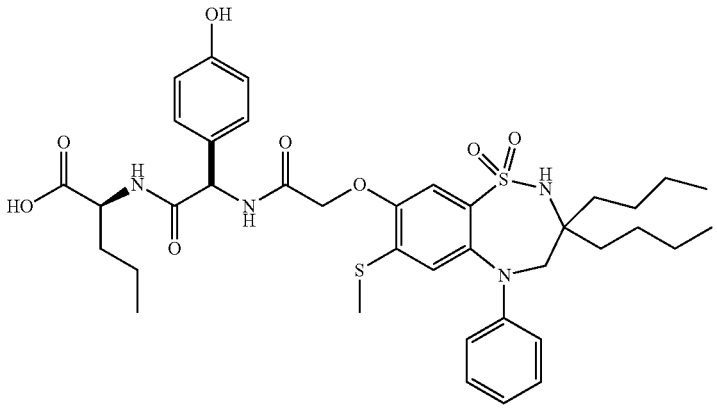 [SMILES: CCCCC1(CCCC)CN(c2ccccc2)c2cc(SC)c(OCC(=O)N[C@@H](C(=O)N[C@@H](CCC)C(=O)O)c3ccc(O)cc3)cc2S(=O)(=O)N1] | 67 | — |
| 10. | 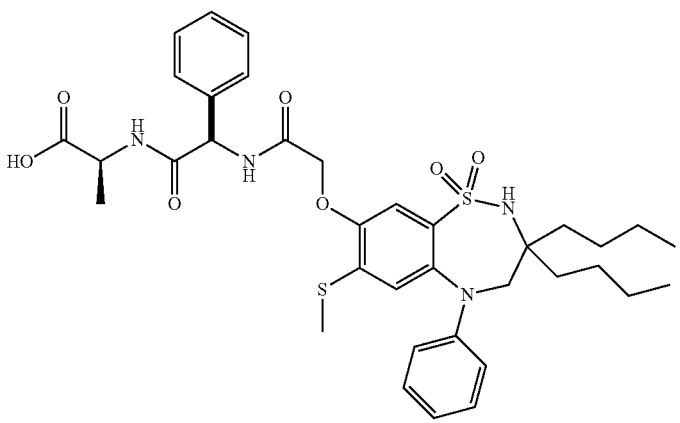 [SMILES: CCCCC1(CCCC)CN(c2ccccc2)c2cc(SC)c(OCC(=O)N[C@@H](C(=O)N[C@@H](C)C(=O)O)c3ccccc3)cc2S(=O)(=O)N1] | 68 | 0.2 |

TABLE 1-continued

| Example | Structure | % inhibition 0.156 μmol/kg | Mean IC50 nM |
|---|---|---|---|
| 11. | 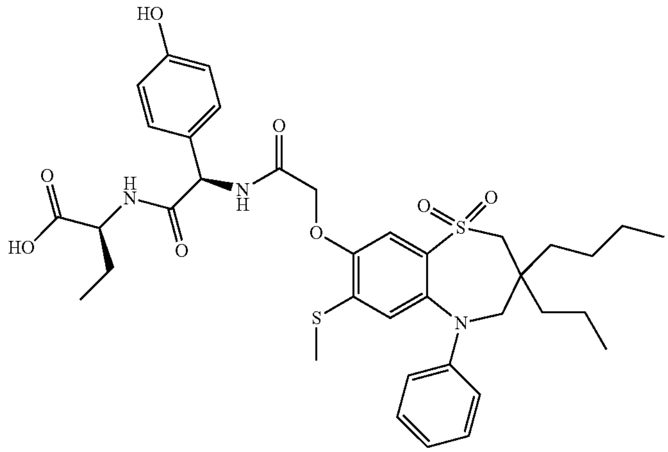 [SMILES: CCCCC1(CCC)CN(c2ccccc2)c2cc(SC)c(OCC(=O)N[C@@H](C(=O)N[C@@H](CC)C(=O)O)c3ccc(O)cc3)cc2S(=O)(=O)C1] | 63 | 0.15 |
| 12. | 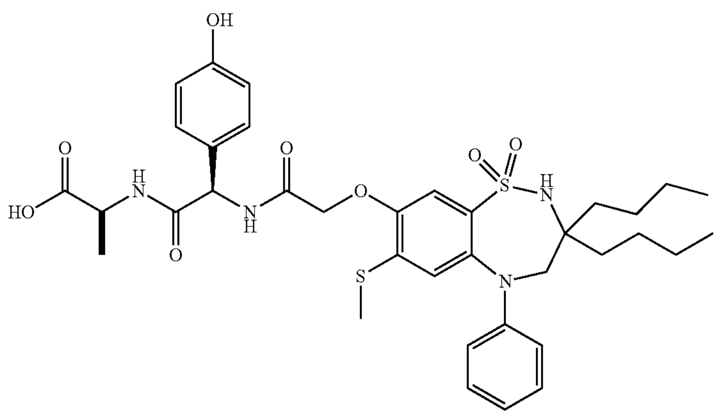 [SMILES: CCCCC1(CCCC)CN(c2ccccc2)c2cc(SC)c(OCC(=O)N[C@@H](C(=O)N[C@@H](C)C(=O)O)c3ccc(O)cc3)cc2S(=O)(=O)N1] | 63 | 0.3 |
| 13. | 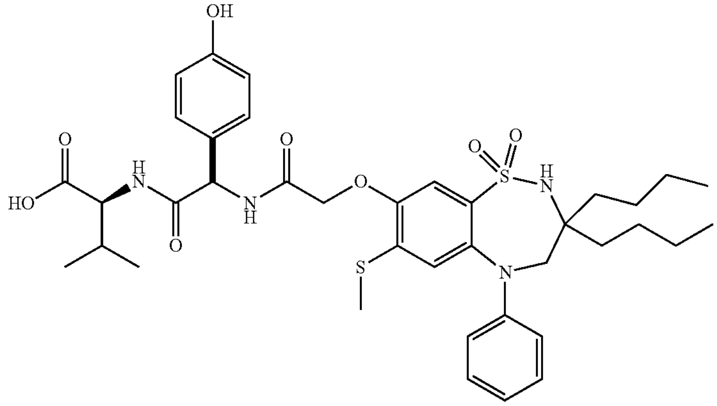 [SMILES: CCCCC1(CCCC)CN(c2ccccc2)c2cc(SC)c(OCC(=O)N[C@@H](C(=O)N[C@H](C(=O)O)C(C)C)c3ccc(O)cc3)cc2S(=O)(=O)N1] | 68 | 0.13 |

TABLE 1-continued

| Example | Structure | % inhibition 0.156 μmol/kg | Mean IC50 nM |
|---|---|---|---|
| 14. | 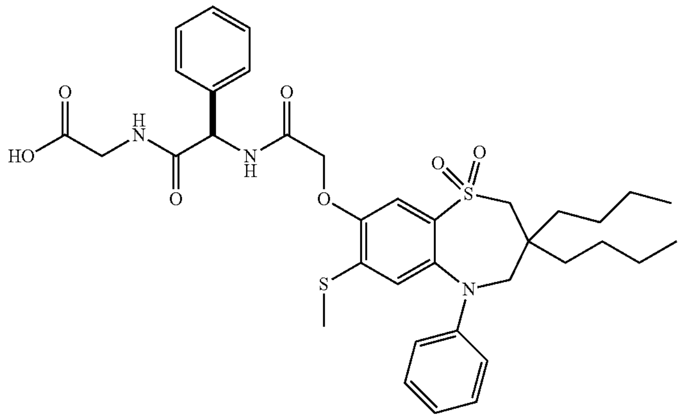 [SMILES: CCCCC1(CCCC)CN(c2ccccc2)c2cc(SC)c(OCC(=O)N[C@@H](C(=O)NCC(=O)O)c3ccccc3)cc2S(=O)(=O)C1] | 28 | 1.2 |

Example 16

In Vivo Animal Model of Primary Sclerosing Cholangitis (PSC)

A genetic mice with targeted disruption of the Multidrug resistant Mdr2 (Abcb4) gene encoding a canalicular phospholipid flippase (Mdr2−/−mice) spontaneously develop sclerosing cholangitis with macroscopic and microscopic features of human Primary sclerosing cholangitis. Bile duct injury in these mice is linked to defective biliary phospholipid secretion resulting in an increased concentration of free non-micellar bile acids which subsequently cause bile duct epithelial cell (cholangiocyte) injury, pericholangitis, periductal fibrosis with ductular proliferation and finally sclerosing cholangitis. Gene expression profiling has revealed remarkable similarities between Mdr2−/− and human PSC. In analogy to the Mdr2−/− mouse model of sclerosing cholangitis, Multidrug resistant protein MDR3/ABCB4 (the human orthologue of rodent Mdr2/Abcb4) defects play a role in the pathogenesis of various cholangiopathies in humans. MDR3 variants play a role as a modifier gene in the pathogenesis of various cholangiopathies such as PSC, Primary Biliary cirrhosis (PBC) and adulthood idiopathic ductopenia/biliary fibrosis.

Mdr2−/− mice were given daily oral doses of the compound of Example 14 by gavage for 2-4 weeks and controls were dosed the vehicle in the same way. Serum liver tests, liver histology and fibrosis were investigated. The compound of Example 14 improves liver tests, liver histology and fibrosis.

Example 17

A formulation for delayed release of the IBAT inhibitor having the following composition is be prepared:

| Substance | amount/capsule (mg) |
|---|---|
| IBAT inhibitor compound Example 14 | 10 |
| Non pareil spheres | 500 |
| Ethyl cellulose | 2 |
| Hydroxypropylmethyl cellulose | 10 |
| Eudragit L100-55, CAS No: 25212-88-8 | 25 |
| Triethylcitrate | 2.4 |

The IBAT inhibitor compound of Example 14 is dissolved together with ethyl cellulose and hydroxypropyl cellulose in ethanol 99%. The mixture is then sprayed onto the non-pareil spheres in a fluidized bed apparatus. Thereafter, the pellets are dried and aerated to remove residual ethanol. The Eudragit L100-55 dispersion with addition of triethyl citrate is then sprayed onto the drug beads in a fluidized bed apparatus. Subsequently, the coated beads are filled in hard gelatine capsules after drying and sieving.

Example 18

A formulation for delayed release of the IBAT inhibitor having the following composition is prepared:

| Ingredient | amount/tablet (mg) |
|---|---|
| IBAT inhibitor compound Example 14 | 10 |
| Silicon dioxide | 200 |
| Povidone K-25 | 20 |
| Eudragit FS30D, CAS no: 26936-24-3 | 30 |
| Microcrystalline cellulose | 250 |
| Sodium stearyl fumarate | 5 |

The IBAT inhibitor compound of Example 14 is suspended in water and sprayed onto silicon dioxide cores of a predefined size in a fluidized bed apparatus. The drug pellets are dried in an oven at 40° C. for 24 h. Thereafter, a layer of Povidone K-25 is applied on the beads from an ethanolic solution in a fluidized bed apparatus. A final coat of Eudragit FS30D dispersion is applied thereafter in a fluidized bed. The coated beads are mixed with microcrystalline cellulose and sodium stearyl fumarate in a mixer and subsequently compressed to tablets.

Example 19

An IBAT inhibitor—colesevelam combination tablet with immediate release of the IBAT inhibitor and colon release of the bile acid binder having the following composition is prepared:

| Ingredient | amount/tablet (mg) |
|---|---|
| Core | |
| Colesevelam hydrochloride | 400 |
| Microcrystalline cellulose | 150 |
| Hydroxypropylmethyl cellulose | 50 |
| Colloidal silicon dioxide | 10 |
| Magnesium stearate | 5 |
| Colon release layer | |
| Eudragit FS30D | 60 |
| PlasACRYL T20, CAS no 123-94-4 | 6 |
| IBAT inhibitor layer | |
| IBAT inhibitor Example 14 | 7 |
| Hydroxypropylmethyl cellulose | 12 |
| Croscarmellose sodium | 6 |
| Protective coating | |
| Hydroxypropylmethyl cellulose | 12 |
| Polyethylene glycol | 2 |

Colesevelam hydrochloride, microcrystalline cellulose and colloidal silicon dioxide are mixed and granulated with hydroxypropyl methyl cellulose dissolved in water. The granules are dried and mixed with magnesium stearate and compressed to tablets. The EUDRAGIT FS30D dispersion and water are stirred into the PlasACRYL T20 and sprayed onto the core tablets using a suitable coating machine. The IBAT inhibitor coating suspension is prepared by mixing the IBAT inhibitor, hydroxypropyl methyl cellulose and croscarmellose sodium in water and sprayed onto the tablet cores with the colon release layer using a suitable coating machine. Finally the protective coating solution of hydroxypropylmethyl cellulose and polyethylene glycol are sprayed onto the tablets using a suitable coating machine.

Example 20

A Colesevelam colon release tablet having the following composition is prepared:

| Ingredient | amount/tablet (mg) |
|---|---|
| Core | |
| Colesevelam hydrochloride | 400 |
| Microcrystalline cellulose | 150 |
| Hydroxypropyl methyl cellulose | 50 |
| Colloidal silicon dioxide | 10 |
| Magnesium stearate | 5 |
| Colon release layer | |
| Amylose | 30 |
| Eudragit S100 | 60 |
| Triethylcitrate | 6 |
| Glycerolmonostearate | 3 |

Colesevelam hydrochloride, microcrystalline cellulose and colloidal silicon dioxide are mixed and granulated with hydroxypropyl methyl cellulose dissolved in water. The granules are dried and mixed with magnesium stearate and compressed to tablets. Amylose, Eudragit 100, triethylcitrate and glycerolmonosterate are dissolved in suitable solvents and sprayed onto the tablet cores using a suitable coating machine.

The invention claimed is:

1. A method for treating cholestasis in a subject, the method comprising orally administering to a subject in need of such treatment a therapeutically effective amount an IBAT inhibitor, wherein the IBAT inhibitor is 1,1-dioxo-3,3-dibutyl-5-phenyl-7-methylthio-8-(N—{(R)-α-[N—((S)-1-carboxypropyl)carbamoyl]-4-hydroxybenzyl}carbamoylmethoxy)-2,3,4,5-tetrahydro-1,2,5-benzothiadiazepine, or a pharmaceutically acceptable salt thereof.

2. The method of claim 1, wherein the subject has pruritus as a symptom of cholestasis.

3. The method of claim 1, wherein treatment of cholestasis decreases the level of serum bile acids in the subject.

4. The method of claim 1, wherein treatment of cholestasis decreases the level of liver bile acids in the subject.

5. The method of claim 1, wherein the subject is diagnosed with a bile acid disease.

6. The method of claim 1, wherein the cholestasis is cholestasis of pregnancy.

7. The method of claim 1, wherein the subject is a pediatric subject.

8. The method of claim 5, wherein the bile acid disease is selected from the group consisting of Alagilles syndrome (ALGS), progressive familial intrahepatic cholestasis (PFIC), primary biliary cirrhosis (PBC), liver fibrosis, non alcoholic fatty liver disease, non-alcoholic steatohepatitis (NASH), and primary sclerosing cholangitis (PSC).

* * * * *

UNITED STATES PATENT AND TRADEMARK OFFICE
CERTIFICATE OF CORRECTION

PATENT NO. : 10,093,697 B2
APPLICATION NO. : 15/726203
DATED : October 9, 2018
INVENTOR(S) : Per-Göran Gillberg, Hans Graffner and Ingemar Starke Page 1 of 1

It is certified that error appears in the above-identified patent and that said Letters Patent is hereby corrected as shown below:

In the Claims

In Claim 1, at Column 44, Line 24, please delete "effective amount an" and insert -- effective amount of an --, therefor.

In Claim 8, at Column 44, Line 42, please delete "Alagilles syndrome" and insert -- Alagille syndrome --, therefor.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*